(12) United States Patent
Wang et al.

(10) Patent No.: US 12,398,137 B2
(45) Date of Patent: Aug. 26, 2025

(54) COMPOSITIONS PROVIDING SLOW RELEASE OF CAFFEINE

(71) Applicant: PepsiCo, Inc., Purchase, NY (US)

(72) Inventors: Yu Wang, New York, NY (US); DaSom No, White Plains, NY (US); Yuan Fang, Cortlandt Manor, NY (US); Nelson Trusler, Cortlandt Manor, NY (US); Damian Browne, Old Greenwich, CT (US); George Meyer, White Plains, NY (US); Xin Zhao, Shanghai (CN); Meng Tian, Luoyang (CN); Shiyi Zhang, Shanghai (CN)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 17/843,197

(22) Filed: Jun. 17, 2022

(65) Prior Publication Data
US 2022/0411424 A1 Dec. 29, 2022

(30) Foreign Application Priority Data

Jun. 17, 2021 (CN) .............................. 202110670135

(51) Int. Cl.
C07C 59/265 (2006.01)
A23B 70/10 (2025.01)
A23L 2/38 (2021.01)
A23L 2/52 (2006.01)
A23L 2/68 (2006.01)
A23L 2/72 (2006.01)
A23L 27/12 (2016.01)
A23L 29/10 (2016.01)
A23L 29/25 (2016.01)
A23L 33/105 (2016.01)
C07D 309/10 (2006.01)
C07D 473/12 (2006.01)

(52) U.S. Cl.
CPC ............ *C07D 473/12* (2013.01); *A23B 70/10* (2025.01); *A23L 2/68* (2013.01); *A23L 2/72* (2013.01); *A23L 27/12* (2016.08); *A23L 29/25* (2016.08); *C07C 59/265* (2013.01); *C07D 309/10* (2013.01)

(58) Field of Classification Search
CPC .... C07D 473/12; C07D 309/10; A23B 70/10; A23L 2/52; A23L 2/68; A23L 2/72; A23L 2/38; A23L 27/12; A23L 29/25; A23L 29/10; A23L 33/105; A23L 35/10; C07C 59/265; A23V 2002/00
See application file for complete search history.

(56) References Cited

U.S. PATENT DOCUMENTS

| | | |
|---|---|---|
| 2,181,549 A | 11/1939 | Theodor |
| 2,753,371 A | 7/1956 | Barnes |
| 2,963,368 A | 12/1960 | Greenbaum |
| 4,004,038 A | 1/1977 | Wickremasinghe |
| 4,248,789 A | 2/1981 | Okada |
| 4,315,036 A | 2/1982 | Husaini et al. |
| 5,518,730 A | 5/1996 | Fuisz |
| 5,597,580 A | 1/1997 | Sickler, Jr. |
| 5,811,101 A | 9/1998 | Waltman |
| 5,902,628 A | 5/1999 | Shamil |
| 6,265,012 B1 | 7/2001 | Shamil |
| 6,339,116 B1 | 1/2002 | Afzali-Ardakani et al. |
| 6,723,369 B2 | 4/2004 | Burgess |
| 7,032,745 B2 | 4/2006 | Saulle |
| 7,056,547 B2 | 6/2006 | Ogura et al. |
| 7,825,169 B2 | 11/2010 | Wada et al. |
| 7,989,009 B2 | 8/2011 | Kandaswami et al. |
| 8,029,770 B2 | 10/2011 | Lu et al. |
| 8,043,645 B2 | 10/2011 | Robinson et al. |
| 8,097,286 B2 | 1/2012 | Samuel et al. |
| 8,394,782 B2 | 3/2013 | Stroumpoulis et al. |
| 8,435,576 B2 | 5/2013 | Troplin et al. |
| 8,513,216 B2 | 8/2013 | Stroumpoulis et al. |
| 8,563,051 B2 | 10/2013 | Samuel et al. |
| 8,697,171 B2 | 4/2014 | Iwasaki et al. |
| 8,853,184 B2 | 10/2014 | Stroumpoulis et al. |
| 9,365,335 B2 | 6/2016 | Burgess et al. |
| 9,387,227 B2 | 7/2016 | Gee |
| 9,840,521 B2 | 12/2017 | Zaworotko et al. |
| 10,149,850 B2 | 12/2018 | Mishra et al. |
| 10,266,322 B2 | 4/2019 | Hauck |
| 10,376,521 B2 | 8/2019 | Zaworotko et al. |
| 10,624,830 B2 | 4/2020 | Deng et al. |
| 10,842,797 B2 | 11/2020 | Zaworotko et al. |
| 10,881,118 B2 | 1/2021 | Guttapadu et al. |
| 10,925,911 B2 | 2/2021 | Ziegenfuss et al. |
| 10,945,953 B1 | 3/2021 | Moaseri |
| 11,020,401 B2 | 6/2021 | Mishra et al. |
| 2001/0008891 A1 | 7/2001 | Subbiah |
| 2003/0039619 A1 | 2/2003 | Bunger et al. |
| 2003/0211184 A1 | 11/2003 | Hoving et al. |
| 2004/0224906 A1 | 11/2004 | Hoving et al. |

(Continued)

FOREIGN PATENT DOCUMENTS

| | | |
|---|---|---|
| AU | 2006318700 A1 | 5/2007 |
| AU | 2019271387 A1 | 1/2021 |

(Continued)

OTHER PUBLICATIONS

International Search Report and Written Opinion for International Application No. PCT/US2022/033988 mailed Sep. 2, 2022, 8 pages.

(Continued)

*Primary Examiner* — Sun Jae Yoo
(74) *Attorney, Agent, or Firm* — Sterne, Kessler, Goldstein & Fox P.L.L.C.

(57) ABSTRACT

The present disclosure relates to complexes comprising caffeine and tannic acid as well as emulsions and beverages comprising these complexes which slow the release of the caffeine. Also described are methods of preparing the complexes and emulsions and beverages comprising caffeine-tannic acid complexes.

18 Claims, 16 Drawing Sheets

(56) References Cited

U.S. PATENT DOCUMENTS

| | | |
|---|---|---|
| 2004/0258765 A1 | 12/2004 | Gee |
| 2005/0207998 A1 | 9/2005 | Lu et al. |
| 2006/0024385 A1 | 2/2006 | Pedersen |
| 2007/0258920 A1 | 11/2007 | Lecoupeau et al. |
| 2008/0261897 A1 | 10/2008 | Dorr et al. |
| 2009/0004360 A1 | 1/2009 | Bingley et al. |
| 2009/0018186 A1 | 1/2009 | Chen et al. |
| 2009/0035440 A1 | 2/2009 | Velikov |
| 2010/0143573 A1 | 6/2010 | Godber et al. |
| 2010/0166851 A1 | 7/2010 | Dallas |
| 2010/0204204 A1 | 8/2010 | Zaworotko et al. |
| 2010/0227874 A1 | 9/2010 | Chou et al. |
| 2011/0207761 A1 | 8/2011 | Losev et al. |
| 2011/0318474 A1* | 12/2011 | Berry .................... A23D 9/007 426/631 |
| 2012/0269913 A1 | 10/2012 | Chu et al. |
| 2013/0149359 A1 | 6/2013 | Sanders |
| 2013/0261136 A1 | 10/2013 | Chu et al. |
| 2014/0113054 A1 | 4/2014 | Sharp |
| 2014/0271527 A1 | 9/2014 | Moreadith et al. |
| 2015/0336981 A1 | 11/2015 | Orchard-Jardine et al. |
| 2016/0249634 A1 | 9/2016 | Shiono et al. |
| 2016/0330991 A1 | 11/2016 | Nishitani et al. |
| 2017/0119772 A1 | 5/2017 | Lee et al. |
| 2018/0140709 A1 | 5/2018 | Chancey |
| 2018/0184692 A1 | 7/2018 | Nachbagauer et al. |
| 2018/0344650 A1 | 12/2018 | Singh et al. |
| 2019/0105326 A1 | 4/2019 | Mishra et al. |
| 2020/0276203 A1 | 9/2020 | Larocca et al. |
| 2020/0306252 A1 | 10/2020 | Sheu |
| 2020/0359829 A1 | 11/2020 | Light |
| 2020/0383349 A1 | 12/2020 | Wan et al. |
| 2022/0401449 A1 | 12/2022 | Wang et al. |

FOREIGN PATENT DOCUMENTS

| | | |
|---|---|---|
| CN | 1039705 A | 2/1990 |
| CN | 102318714 A | 1/2012 |
| EP | 2369939 B1 | 2/2015 |
| FR | 1003627 A | 3/1952 |
| JP | 2003313775 A | 11/2003 |
| JP | 2014108106 A | 6/2014 |
| WO | WO-9324154 A1 | 12/1993 |
| WO | WO-9711109 A1 | 3/1997 |
| WO | WO-9742957 A1 | 11/1997 |
| WO | WO-9820753 A1 | 5/1998 |
| WO | WO-0062628 A1 | 10/2000 |
| WO | WO-0111988 A2 | 2/2001 |
| WO | WO-0214251 A1 | 2/2002 |
| WO | WO-2005000032 A1 | 1/2005 |
| WO | WO-2006079731 A2 | 8/2006 |
| WO | WO-2007056133 A2 | 5/2007 |
| WO | WO-2008141333 A1 | 11/2008 |
| WO | WO-2008153945 A2 | 12/2008 |
| WO | WO-2009015996 A2 | 2/2009 |
| WO | WO-2009016018 A1 | 2/2009 |
| WO | WO-2009073437 A1 | 6/2009 |
| WO | WO-2010076112 A2 | 7/2010 |
| WO | WO-2011011418 A1 | 1/2011 |
| WO | WO-2011059909 A1 | 5/2011 |
| WO | WO-2011074538 A1 | 6/2011 |
| WO | WO-2012051287 A1 | 4/2012 |
| WO | WO-2012087267 A2 | 6/2012 |
| WO | WO-2012090505 A1 | 7/2012 |
| WO | WO-2013000653 A1 | 1/2013 |
| WO | WO-2013067199 A1 | 8/2013 |
| WO | WO-2014059228 A1 | 4/2014 |
| WO | WO-2014071438 A1 | 5/2014 |
| WO | WO-2014150967 A1 | 9/2014 |
| WO | WO-2014172650 A1 | 10/2014 |
| WO | WO-2014178214 A1 | 11/2014 |
| WO | WO-2015064168 A1 | 5/2015 |
| WO | WO-2015127063 A1 | 8/2015 |
| WO | WO-2016112170 A1 | 7/2016 |
| WO | WO-2017009813 A1 | 1/2017 |
| WO | WO-2017070501 A1 | 4/2017 |
| WO | WO-2018012196 A1 | 1/2018 |
| WO | WO-2018012197 A1 | 1/2018 |
| WO | WO-2018025504 A1 | 2/2018 |
| WO | WO-2018027070 A1 | 2/2018 |
| WO | WO-2018027127 A1 | 2/2018 |
| WO | WO-2018098134 A1 | 5/2018 |
| WO | WO-2018100864 A1 | 6/2018 |
| WO | WO-2018122383 A1 | 7/2018 |
| WO | WO-2018168669 A1 | 9/2018 |
| WO | WO-2019099531 A1 | 5/2019 |
| WO | WO-2019108450 A1 | 6/2019 |
| WO | WO-2019140406 A1 | 7/2019 |
| WO | WO-2019221015 A1 | 11/2019 |
| WO | WO-2019224381 A1 | 11/2019 |
| WO | WO-2019230013 A1 | 12/2019 |
| WO | WO-2020132855 A1 | 7/2020 |
| WO | WO-2020132860 A1 | 7/2020 |
| WO | WO-2020175378 A1 | 9/2020 |
| WO | WO-2020181212 A1 | 9/2020 |
| WO | WO-2021038830 A1 | 3/2021 |
| WO | WO-2021056248 A1 | 4/2021 |
| WO | WO-2021114024 A1 | 6/2021 |
| WO | WO-2022266441 A1 | 12/2022 |

OTHER PUBLICATIONS

International Search Report and Written Opinion for International Application No. PCT/US2022/033989 mailed Sep. 9, 2022, 8 pages.

Magkos, F., et al., "Caffeine Use in Sports, Pharmacokinetics in Man, and Cellular Mechanisms of Action," Critical Reviews in Food Science and Nutrition 45(7-8):535-62, Taylor & Francis Group, United States (2005).

* cited by examiner

COMPOSITIONS PROVIDING SLOW RELEASE OF CAFFEINE

FIELD

The present disclosure relates to complexes comprising caffeine and tannic acid and emulsions comprising these complexes. The complexes slow the release of caffeine when used in a beverage. Also described are methods of preparing a beverage comprising tannic acid and caffeine complexes.

BACKGROUND

Caffeine is one of the most widely used pharmacologically active compounds. Previous studies have determined that it is absorbed by the gastrointestinal tract, with peak concentrations occurring between 15 and 120 minutes following ingestion ("Caffeine use in sports, pharmacokinetics in man, and cellular mechanisms of action," Crit Rev Food Sci Nutr. 2005; 45(7-8); 535-62). Extending the release of caffeine from beverages such as soft drinks allows the body to progressively absorb it which can avoid jitteriness and the "caffeine crash."

SUMMARY

In a first aspect, the present disclosure provides a complex comprising caffeine and tannic acid. In a first embodiment of the first aspect, the weight/weight ratio of caffeine to tannic acid in the complex is from about 10:1 to about 1:10. In a second embodiment of the first aspect, the weight/weight ratio of caffeine to tannic acid in the complex is from about 5:1 to about 1:5. In a third embodiment of the first aspect, the weight/weight ratio of caffeine to tannic acid in the complex is from about 4:1 to about 1:4. In a fifth embodiment of the first aspect, the weight percent of caffeine in the complex is from about 23% to about 35%. In a sixth embodiment of the first aspect, the weight percent of caffeine in the complex is from about 35% to about 53%.

In a seventh embodiment of the first aspect, the complex comprises an additional compound selected from the group consisting of citric acid, dopamine, maleic acid, malonic acid, and oxalic acid.

In a second aspect, the present disclosure provides an emulsion comprising an oil phase comprising at least one oil comprising a complex comprising caffeine and tannic acid; and an aqueous phase comprising water. In a first embodiment of the second aspect, the emulsion further comprises one or more stabilizers. In a second embodiment of the second aspect, the emulsion further comprises one or more emulsifiers.

In a third embodiment of the second aspect, the emulsion further comprises from about 2 wt % to about 30 wt % of the at least one oil. In a fourth embodiment of the second aspect, the emulsion comprises about 5 wt % to about 10 wt % of the at least one oil. In a fifth embodiment of the second aspect, the at least one oil is selected from the group consisting of one or more edible oils, one or more edible waxes, and combinations thereof. In a sixth embodiment of the second aspect, the at least one oil is selected from the group consisting of ghee, mustard oil, olive oil, rice bran oil, flaxseed oil, groundnut oil, sesame oil, almond oil, cashew oil, canola oil, soybean oil, avocado oil, walnut oil, grapeseed oil, sunflower oil, medium chain triglycerides, coconut oil, palm kernel oil, carnuba wax, beeswax, paraffin wax, rice bran wax, candelilla wax, sunflower wax, sugarcane wax, propolis wax, shellac wax, and combinations thereof.

In a seventh embodiment of the second aspect, the at least one oil is selected from the group consisting of sunflower oil and medium chain triglycerides.

In an eighth embodiment of the second aspect, the emulsion comprises from about 0.1 wt % to about 15 wt % of the complex. In a ninth embodiment, the emulsion comprises from about 1 wt % to about 4 wt % of the complex.

In a tenth embodiment, the emulsion comprises from about 0.002 wt % to about 8 wt % of the one or more stabilizers. In an eleventh embodiment of the second aspect, the emulsion comprises from about 0.08 wt % to about 1.2 wt % of the one or more stabilizers. In a twelfth embodiment of the second aspect, the one or more stabilizers is selected from the group consisting of sorbitan trioleate, stearic acid, ethyl cellulose, polyglycerol polyricinoleate, sucrose, and combinations thereof. In a thirteenth embodiment of the second aspect, the one or more stabilizers is selected from the group consisting of sorbitan trioleate, stearic acid, ethyl cellulose, polyglycerol polyricinoleate, and combinations thereof.

In a fourteenth embodiment of the second aspect, the emulsion comprises from about 4 wt % to about 40 wt % of the one or more emulsifiers. In a fifteenth embodiment of the second aspect, the emulsion comprises about 10 wt % of the one or more emulsifiers. In a sixteenth embodiment of the second aspect, the one or more emulsifiers is selected from the group consisting of agar, carrageenan, gellan, gelatin, guar gum, sodium alginate, xanthan gum, gum Arabic, *Quillaja saponaria* saponins, and combinations thereof. In a seventeenth embodiment of the second aspect, the one or more stabilizers is gum Arabic.

In a third aspect, the present disclosure provides a process for preparing a complex comprising caffeine and tannic acid, the process comprising adding tannic acid and caffeine to ethanol or aqueous ethanol and spray drying the resulting solution.

In a fourth aspect, the present disclosure provides a process for preparing a complex comprising caffeine and tannic acid, the process comprising adding an aqueous solution of tannic acid in water to an aqueous solution of caffeine in water and filtering the resulting suspension.

In a fifth aspect, the present disclosure provides a process for preparing an emulsion comprising a complex comprising caffeine and tannic acid, the process comprising adding a mixture of the complex, at least one oil, and optionally one or more stabilizers to a mixture of water and, optionally, one or more emulsifiers; and mixing at high speed.

In a sixth aspect, the present disclosure provides a beverage comprising an emulsion comprising a complex comprising caffeine and tannic acid.

BRIEF DESCRIPTION OF THE DRAWINGS

The present disclosure is illustrated by way of example, and not limited by, the accompanying figures.

DETAILED DESCRIPTION

Definitions

Figure 1A:
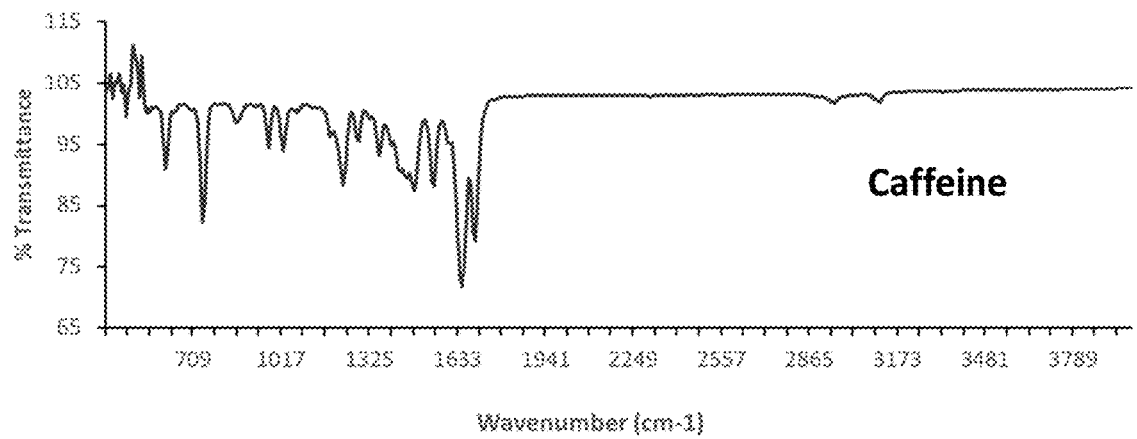
FIG. 1A depicts the FT IR spectrum of caffeine.
Figure 1B:
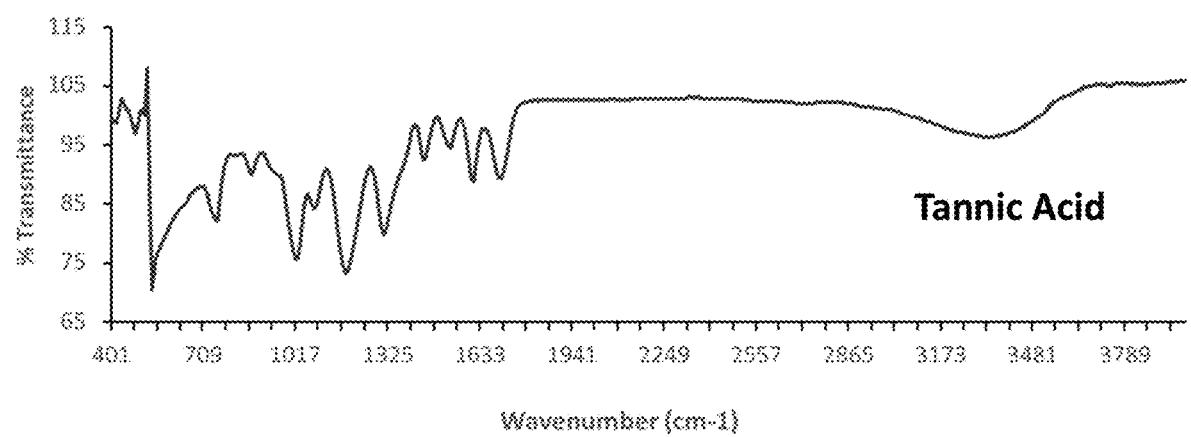
FIG. 1B depicts the FT IR spectrum of tannic acid.
Figure 2A:
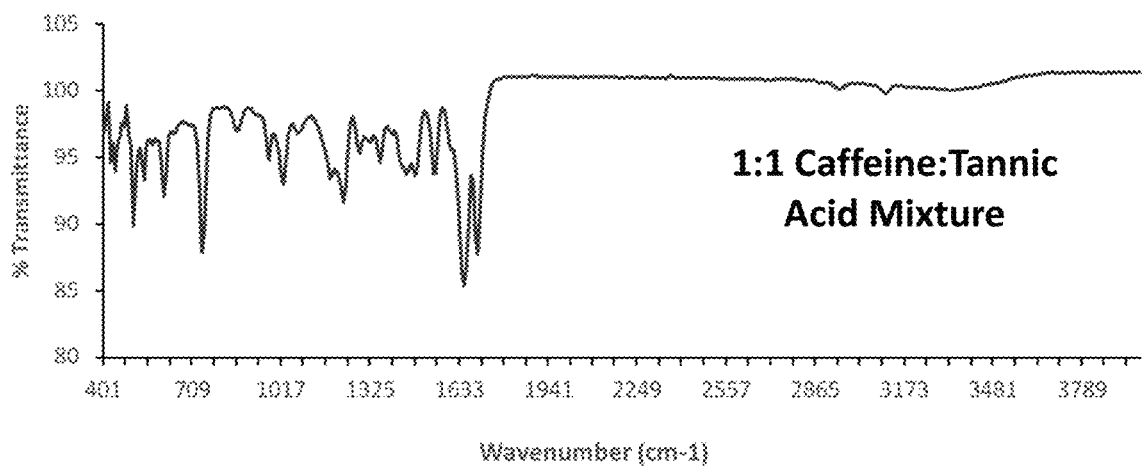
FIG. 2A depicts the FT IR spectrum of a 1:1 mixture of caffeine and tannic acid.
Figure 2B:
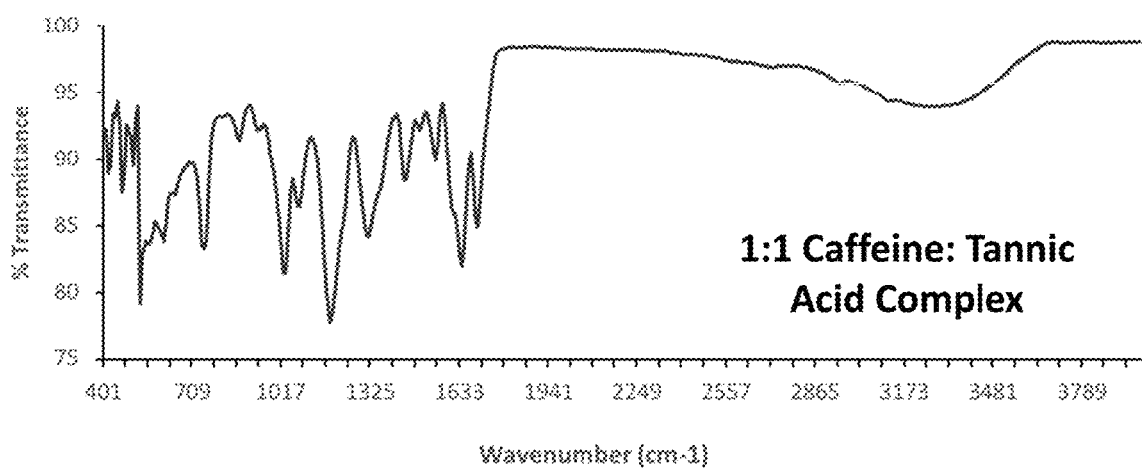
FIG. 2B depicts the FT IR spectrum of a complex comprising a 1:1 wt/wt ratio of tannic acid:caffeine.
Figure 3:
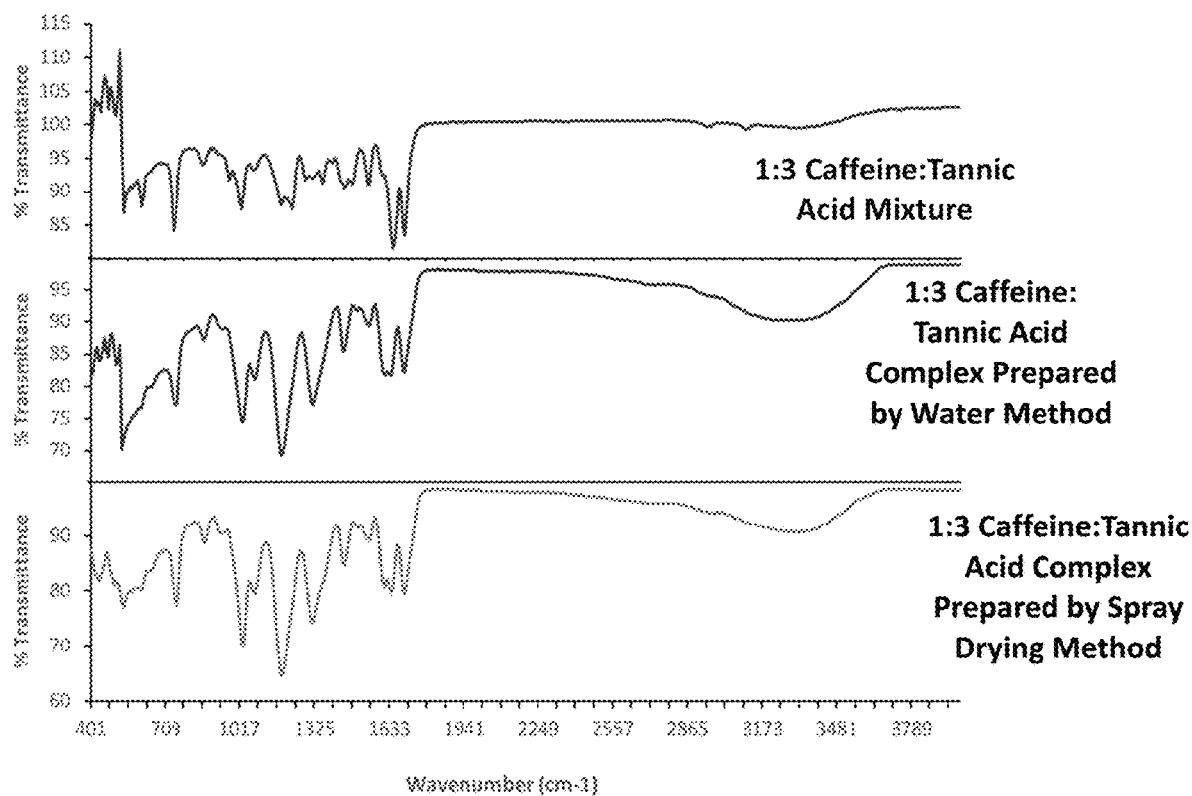
FIG. 3 depicts the FT IR spectra of a 1:3 mixture of caffeine and tannic acid, a complex comprising a 1:3 wt/wt ratio of caffeine:tannic acid as prepared through an aqueous precipitation method, and a complex comprising a 1:3 wt/wt ratio of caffeine:tannic acid that has been spray dried.

The singular forms "a," "an," and "the" include plural referents unless the context clearly dictates otherwise.

As used herein, the term "or" is a logical disjunction (i.e., and/or) and does not indicate an exclusive disjunction unless expressly indicated as such with the terms "either," "unless," "alternatively," and words of similar effect.

As used herein, the term "about" refers to ±10% of the noted value, unless otherwise specified, and unless the upper bound of the range would exceed 100% of the composition, in which case the upper limit of the range is limited to 99.9%. Thus, and by way of example only, a composition including about 10 weight percent of a given ingredient could have from 9 to 11 weight percent of the compound. Similarly, a composition including about 95 weight percent of a given ingredient could have from 85.5 to 99.9 weight percent of the ingredient in the composition.

As used herein, "beverage" refers to edible formulations suitable for drinking. Examples of beverages include, but are not limited to, soft drinks, fountain beverages, frozen ready-to-drink beverages, coffee beverages, tea beverages, sport drinks, juices, dairy beverages, and alcoholic beverages. Beverages can be carbonated or noncarbonated and can be clear, i.e. transparent, semi-transparent, or opaque. As used herein, "fountain beverages" refer to beverages prepared by combining a beverage syrup and water, which can be optionally carbonated, at or just prior to the point of consumption.

As used herein, the term "emulsifier" refers to an agent that allows an aqueous phase and an oil phase to be blended into an emulsion. Examples of suitable emulsifiers include, but are not limited to, agar, carrageenan, protein derived emulsifiers (for example, whey protein isolate and sodium caseinate), gellan, gelatin, guar gum, sodium alginate, xanthan gum, gum Arabic, *Quillaja saponaria* saponins, and combinations thereof. Additional examples of emulsifying agents will be apparent to those skilled in the art of food or beverage formulations, given the benefit of this disclosure.

As used herein, the term "stabilizer" refers an agent that stabilizes the caffeine-tannic acid complex in the one or more oils of the emulsions described herein. Exemplary stabilizers include, but are not limited to, sorbitan trioleate, stearic acid, ethyl cellulose, polyglycerol polyricinoleate, sucrose, and combinations thereof. Additional examples of stabilizers will be apparent to those skilled in the art of food or beverage formulations, given the benefit of this disclosure.

All percentages provided in this specification are percentages by weight, unless specifically indicated otherwise.

Caffeine-Tannic Acid Complex

The present disclosure provides a complex comprising caffeine and tannic acid. In certain embodiments, the weight/weight ratio of caffeine to tannic acid in the complex can be from about 10:1 to about 1:10. In some embodiments, the weight/weight ratio of caffeine to tannic acid in the complex can be from about 9:1 to about 1:9. In some embodiments, the weight/weight ratio of caffeine to tannic acid in the complex can be from about 8:1 to about 1:8. In some embodiments, the weight/weight ratio of caffeine to tannic acid in the complex can be from about 7:1 to about 1:7. In some embodiments, the weight/weight ratio of caffeine to tannic acid in the complex can be from about 6:1 to about 1:6. In certain embodiments, the weight/weight ratio of caffeine to tannic acid in the complex can be from about 5:1 to about 1:5. In some embodiments, the weight/weight ratio of caffeine to tannic acid in the complex can be from about 4:1 to about 1:4. In some embodiments, the weight/weight ratio of caffeine to tannic acid in the complex can be from about 2:1 to about 1:4. In some embodiments, the weight/weight ratio of caffeine to tannic acid in the complex can be from about 2:1 to about 1:3. In certain embodiments, the weight/weight ratio of caffeine to tannic acid in the complex can be about 1:1. In certain embodiments, the weight/weight ratio of caffeine to tannic acid in the complex can be about 1:2. In certain embodiments, the weight/weight ratio of caffeine to tannic acid in the complex can be about 1:3.

In certain embodiments, the weight percent of caffeine in the complex can be from about 5% to about 95%. In some embodiments, the weight percent of caffeine in the complex can be from about 10% to about 90%. In some embodiments, the weight percent of caffeine in the complex can be from about 15% to about 85%. In some embodiments, the weight percent of caffeine in the complex can be from about 20% to about 80%. In some embodiments, the weight percent of caffeine in the complex can be from about 20% to about 70%. In some embodiments, the weight percent of caffeine in the complex can be from about 20% to about 60%. In some embodiments, the weight percent of caffeine in the complex can be from about 20% to about 50%. In some embodiments, the weight percent of caffeine in the complex can be from about 23% to about 35%. In some embodiments, the weight percent of caffeine in the complex can be from about 35% to about 53%. In certain embodiments, the weight percent of caffeine in the complex can be about 5%, about 10%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 69%, about 65%, about 70%, about 75%, about 80%, about 85%, or about 90%.

In certain embodiments, the complex can comprise caffeine, tannic acid, and an additional compound selected from the group consisting of citric acid, dopamine, maleic acid, malonic acid, and oxalic acid. Without being bound by a particular theory, it believed that under the conditions described herein, tannic acid forms hydrogen bonds with the caffeine molecules to provide a stable complex which, when used in a beverage, slows the release of caffeine from the beverage. Formation of a caffeine-tannic acid complex is supported by spectroscopic analysis, such as FT-IR data, which is discussed elsewhere herein. Surprisingly, FT IR spectra of the caffeine-tannic acid complexes differ significantly from the spectra of non-complexed mixtures of caffeine and tannic acid. This data demonstrates that that the caffeine and tannic acid molecules are associated with each other within the complex.

Compositions Comprising the Complex

The present disclosure further provides aqueous emulsions comprising the complexes described herein. When these emulsions are used in a beverage, they provide a slow release of caffeine. Without being bound by a particular theory, it is believed that the emulsion particles encapsulate the caffeine complex and slow the release of free caffeine into the beverage. The emulsions of the present disclosure comprise a caffeine-tannic acid complex, water (as part of an aqueous phase dispersed throughout the emulsion), one or more oils (as part of an oil phase dispersed throughout the emulsion), optionally one or more emulsifiers, and optionally one or more stabilizers. The emulsion can be a water in oil emulsion or an oil in water emulsion. In typical embodiments, the emulsion is an oil in water emulsion.

In certain embodiments, the emulsion can comprise from about 0.1 wt % to about 15 wt % of the complex comprising caffeine and tannic acid. In certain embodiments, the emulsion can comprise from about 0.1 wt % to about 12 wt % of the complex comprising caffeine and tannic acid. In certain embodiments, the emulsion can comprise from about 0.1 wt % to about 10 wt % of the complex comprising caffeine and tannic acid. In some embodiments, the emulsion can comprise from about 0.15 wt % to about 8 wt % of the complex comprising caffeine and tannic acid. In some embodiments, the emulsion can comprise from about 0.2 wt % to about 6 wt % of the complex comprising caffeine and tannic acid. In some embodiments, the emulsion can comprise from about 0.25 wt % to about 5 wt % of the complex comprising caffeine and tannic acid. In some embodiments, the emulsion can comprise from about 0.50 wt % to about 4.5 wt % of the complex comprising caffeine and tannic acid. In some embodiments, the emulsion can comprise from about 0.75 wt % to about 4 wt % of the complex comprising caffeine and tannic acid. In some embodiments, the emulsion can comprise from about 1 wt % to about 3.5 wt % of the complex comprising caffeine and tannic acid. In some embodiments, the emulsion can comprise from about 1.5 wt % to about 3 wt % of the complex comprising caffeine and tannic acid. In some embodiments, the emulsions can comprise about 0.1 wt %, about 0.15 wt %, about 0.2 wt %, 0.25 wt %, about 0.35 wt %, about 0.45 wt %, about 0.55 wt %, about 0.65 wt %, about 0.75 wt %, about 0.80 wt %, about 0.85 wt %, about 0.90 wt %, about 1.0 wt %, about 1.25 wt %, about 1.5 wt %, about 1.75 wt %, about 2.0 wt %, about 2.25 wt %, about 2.5 wt %, about 2.75 wt %, about 3.0 wt %, about 3.25 wt %, about 3.5 wt %, about 3.75 wt %, about 4.0 wt %, about 4.25 wt %, about 4.5 wt %, about 4.75 wt %, about 5 wt %, about 5.25 wt %, about 5.5 wt %, about 5.75 wt %, about 6 wt %, about 6.25%, about 6.5 wt %, about 6.75 wt %, about 7 wt %, about 7.25 wt %, about 7.5 wt %, about 7.75 wt %, about 8 wt %, about 8.25 wt %, about 8.5 wt %, about 8.75 wt %, about 9 wt %, about 9.25 wt %, about 9.5 wt %, about 9.75 wt %, about 10 wt %, about 12 wt %, or about 15 wt % of the complex comprising caffeine and tannic acid.

In some embodiments, the emulsions can comprise an oil phase comprising from about 2 wt % to about 30 wt % of at least one oil. In some embodiments, the emulsions can comprise an oil phase comprising from about 2 wt % to about 25 wt % of at least one oil. In some embodiments, the emulsions can comprise an oil phase comprising from about 2 wt % to about 20 wt % of at least one oil. In some embodiments, the emulsions can comprise an oil phase comprising from about 5 wt % to about 10 wt % of at least one oil. In some embodiments, the emulsions can comprise from about 6 wt % to about 9 wt % of at least one oil. In some embodiments, the emulsions can comprise about 5 wt %, about 5.5%, about 6 wt %, about 6.5 wt %, about 7 wt %, about 7.5%, about 8 wt %, about 8.5%, about 9 wt %, about 9.5%, about 10 wt %, about 15 wt %, about 18 wt %, about 20 wt %, about 23 wt %, about 25 wt %, about 28 wt %, or about 30 wt % of at least one oil.

Typically, and in certain embodiments, the at least one oil can comprise one or more edible oils and/or one or more edible waxes. In some embodiments, the at least one oil can comprise one or more oils selected from the group consisting of ghee, mustard oil, olive oil, rice bran oil, flaxseed oil, groundnut oil, sesame oil, almond oil, cashew oil, canola oil, soybean oil, avocado oil, walnut oil, grapeseed oil, sunflower oil, medium chain triglycerides, coconut oil, palm kernel oil, carnuba wax, beeswax, paraffin wax, rice bran wax, candelilla wax, sunflower wax, sugarcane wax, propolis wax, shellac wax, and combinations thereof. In some embodiments, the at least one oil can comprise sunflower oil or medium chain triglycerides. In some embodiments, the at least one oil can comprise sunflower oil. In some embodiments, the at least one oil can comprise medium chain triglycerides.

Typically, and in certain embodiments, the caffeine-tannic acid complex can be contained within the dispersed oil phase of the emulsion. In certain embodiments, the oil phase can comprise from about 5 wt % to about 50 wt % of the complex comprising caffeine and tannic acid. In some embodiments, the oil phase can comprise about 10 wt % to about 45 wt % of a complex. In some embodiments, the oil phase can comprise about 15 wt % to about 40 wt % of a complex In some embodiments, the oil phase can comprise about 20 wt % to about 35 wt % of a complex. In some embodiments, the oil phase can comprise about 25 wt % to about 35 wt % of a complex comprising caffeine and tannic acid. In some embodiments, the oil phase can comprise about 5 wt %, about 6 wt %, about 7 wt %, about 8 wt %, about 9 wt %, about 10 wt %, about 11 wt %, about 12 st %, about 13 wt %, about 14 wt %, about 15 wt %, about 16 wt %, about 17 wt %, about 18 wt %, about 19 wt %, 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 46 wt %, about 48 wt %, about 49 wt %, or about 50 wt % of the complex comprising caffeine and tannic acid.

The emulsions described herein can further comprise one or more stabilizers. In some embodiments, the emulsion can comprise from about 0.002 wt % to about 8 wt % of one or more stabilizers. In some embodiments, the emulsion can comprise from about 0.002 wt % to about 6 wt % of one or more stabilizers. In some embodiments, the emulsion can comprise from about 0.002 wt % to about 4 wt % of one or more stabilizers. In some embodiments, the emulsion can comprise from about 0.002 wt % to about 2 wt % of one or more stabilizers. In some embodiments, the emulsion can comprise from about 0.003 wt % to about 1.5 wt % of one or more stabilizers. In some embodiments, the emulsion can comprise from about 0.005 wt % to about 1 wt % of one or more stabilizers. In some embodiments, the emulsion can comprise from about 0.01 wt % to about 0.9 wt % of one or more stabilizers. In some embodiments, the emulsion can comprise from about 0.05 wt % to about 0.8 wt % of one or more stabilizers. In some embodiments, the emulsion can comprise from about 0.1 wt % to about 0.8 wt % of one or more stabilizers. In some embodiments, the emulsion can comprise from about 0.2% to about 0.7 wt % of one or more stabilizers. In some embodiments, the emulsion can comprise from about 0.3 wt % to about 0.6 wt % of one or more stabilizers. In some embodiments, the emulsion can comprise about 0.002 wt %, about 0.003 wt %, about 0.004 wt %, about 0.005 wt %, about 0.01 wt %, about 0.05 wt %, about 0.1 wt %, about 0.15 wt %, about 0.2 wt %, about 0.25 wt %, about 0.3 wt %, about 0.35 wt %, about 0.4 wt %, about 0.45 wt %, about 0.5 wt %, about 0.55 wt %, about 0.6 wt %, about 0.65 wt %, about 0.7 wt %, about 0.75 wt %, about 0.8 wt %, about 0.85 wt %, about 0.9 wt %, about 1 wt %, about 1.2 wt %, about 1.4 wt %, about 1.6 wt %, about 1.8 wt %, about 2 wt %, about 3 wt %, about 4 wt %, about 5 wt %, about 6 wt %, about 7 wt %, or about 8 wt % of one or more stabilizers.

In some embodiments, the oil phase of the emulsion can comprise the one or more stabilizers. In certain embodiments, the oil phase can comprise about 0.1 wt % to about 30 wt % of one or more stabilizers. In some embodiments, the oil phase can comprise about 0.1 wt % to about 25 wt % of one or more stabilizers. In some embodiments, the oil phase can comprise about 0.1 wt % to about 20 wt % of one or more stabilizers. In certain embodiments, the oil phase can comprise about 0.1 wt % to about 10 wt % of one or more stabilizers. In some embodiments, the oil phase can comprise about 0.2 wt % to about 9 wt % of one or more stabilizers. In some embodiments, the oil phase can comprise about 0.5 wt % to about 8% of one or more stabilizers. In some embodiments, the oil phase can comprise about 1 wt % to about 8 wt % of one or more stabilizers. In some embodiments, the oil phase can comprise about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.5 wt %, about 2 wt %, about 2.5 wt %, about 3 wt %, about 3.5 wt %, about 4 wt %, about 4.5 wt %, about 5 wt %, about 5.5 wt %, about 6 wt %, about 6.5 wt %, about 7 wt %, about 7.5 wt %, about 8 wt %, about 8.5 wt %, about 9 wt %, about 9.5 wt %, about 10 wt %, about 12 wt %, about 15 wt %, about 20 wt %, about 25 wt %, or about 30 wt % of one or more stabilizers.

In some embodiments, the one or more stabilizers can be selected from the group consisting of sorbitan trioleate, stearic acid, ethyl cellulose, polyglycerol polyricinoleate, sucrose, and combinations thereof.

In some embodiments, the one or more stabilizers can comprise sorbitan trioleate, stearic acid, ethyl cellulose, polyglycerol polyricinoleate, and combinations thereof. In some embodiments, the one or more stabilizers can comprise sorbitan trioleate. In some embodiments, the one or stabilizers can comprise stearic acid. In some embodiments, the one or more stabilizers can comprise ethyl cellulose. In some embodiments, the one or more stabilizers can comprise polyglycerol polyricinoleate. In some embodiments, the one or more stabilizers can comprise a mixture sorbitan trioleate and stearic acid.

The emulsions described herein can also comprise an aqueous phase. In certain aspects, the emulsions can comprise from about 80 wt % to about 98 wt % of an aqueous phase. In some embodiments, the emulsions can comprise from about 85 wt % to about 95% of an aqueous phase. In some embodiments, the emulsions can comprise from about 90 wt % to about 95 wt % of an aqueous phase. In some embodiments, the emulsions can comprise about 91 wt % to about 94 wt % of an aqueous phase. In some embodiments, the emulsions can comprise about 92 wt % of an aqueous phase.

The emulsions described herein can further comprise one or more emulsifiers. In some embodiments, the emulsion can comprise from about 4 wt % to about 40 wt % of one or more emulsifiers. In some embodiments, the emulsion can comprise from about 4 wt % to about 30 wt % of one or more emulsifiers. In some embodiments, the emulsion can comprise from about 4 wt % to about 20 wt % of one or more emulsifiers. In some embodiments, the emulsion can comprise from about 4 wt % to about 15 wt % of one or more emulsifiers. In some embodiments, the emulsion can comprise from about 5 wt % to about 14 wt % of one or more emulsifiers. In some embodiments, the emulsion can comprise from about 6 wt % to about 13 wt % of one or more emulsifiers. In some embodiments, the emulsion can comprise from about 7 wt % to about 12 wt % of one or more emulsifiers. In some embodiments, the emulsion can comprise from about 8% to about 11 wt % of one or more emulsifiers. In some embodiments, the emulsion can comprise about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 20 wt %, about 25 wt %, or about 30 wt % of one or more emulsifiers.

Typically, the aqueous phase can comprise the one or more emulsifiers. In some embodiments, the emulsion can comprise from about 5 wt % to about 40 wt % of one or more emulsifiers. In some embodiments, the emulsion can comprise from about 5 wt % to about 30 wt % of one or more emulsifiers. In some embodiments, the emulsion can comprise from about 5 wt % to about 20 wt % of one or more emulsifiers. In some embodiments, the emulsion can comprise from about 5 wt % to about 15 wt % of one or more emulsifiers. In some embodiments, the aqueous phase can comprise about 6 wt % to about 14 wt % of one or more emulsifiers. In some embodiments, the aqueous phase can comprise about 7 wt % to about 13 wt % of one or more emulsifiers. In some embodiments, the aqueous phase can comprise about 8 wt % to about 12 wt % of one or more emulsifiers. In some embodiments, the aqueous phase can comprise about 9 wt % to about 11 wt % of one or more emulsifiers. In some embodiments, the aqueous phase can comprise about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 20 wt %, about 25 wt %, about 30 wt %, about 35 wt %, or about 40 wt % of one or more emulsifiers.

In some embodiments, the one or more emulsifiers can be selected from the group consisting of agar, carrageenan, gellan, gelatin, guar gum, sodium alginate, xanthan gum, gum Arabic, *Quillaja saponaria* saponins, one or more protein derived emulsifiers (for example, whey protein isolate and/or sodium caseinate) or a mixture thereof. In some embodiments, the one or more emulsifiers can be gum Arabic.

In certain embodiments, the emulsions can comprise a) about 5 wt % to about 30 wt % of at least one oil, wherein the at least one oil comprises from about 20 wt % to about 40 wt % of a complex comprising from about a 10:1 to about a 1:10 wt/wt ratio of caffeine to tannic acid and optionally comprises from about 0.1 wt % to about 10 wt % of one or more stabilizers; and b) an aqueous phase comprising optionally about 5 wt % to about 15 wt % of one or more stabilizers. In some embodiments, the emulsions can comprise a) about 5 wt % to about 30 wt % of at least one oil selected from the group consisting of ghee, mustard oil, olive oil, rice bran oil, flaxseed oil, groundnut oil, sesame oil, almond oil, cashew oil, canola oil, soybean oil, avocado oil, walnut oil, grapeseed oil, sunflower oil, medium chain triglycerides, coconut oil, palm kernel oil, carnuba wax, beeswax, paraffin wax, rice bran wax, candelilla wax, sunflower wax, sugarcane wax, propolis wax, shellac wax, and combinations thereof, wherein the at least one oil comprises about 20 wt % to about 40 wt % of a complex comprising from about a 10:1 to about a 1:10 wt/wt ratio of caffeine to tannic acid and optionally comprises about 0.1 wt % to about 10 wt % of one or more stabilizers selected from the group consisting of sorbitan trioleate, stearic acid, ethyl cellulose, polyglycerol polyricinoleate, sucrose, and combinations thereof; and b) an aqueous phase optionally comprising about 5 wt % to about 15 wt % of one or more emulsifiers selected from the group consisting of agar, carrageenan, gellan, gelatin, guar gum, sodium alginate, xanthan gum, gum Arabic, *Quillaja saponaria* saponins, and combinations thereof.

In certain embodiments, the emulsions can comprise a) about 5 wt % to about 10 wt % of at least one oil, wherein the at least one oil comprises from about 20 wt % to about 40 wt % of a complex comprising from about a 10:1 to about a 1:10 wt/wt ratio of caffeine to tannic acid and optionally comprises from about 0.1 wt % to about 10 wt % of one or more stabilizers; and b) an aqueous phase comprising optionally about 5 wt % to about 15 wt % of one or more stabilizers. In some embodiments, the emulsions can comprise a) about 5 wt % to about 10 wt % of at least one oil selected from the group consisting of ghee, mustard oil, olive oil, rice bran oil, flaxseed oil, groundnut oil, sesame oil, almond oil, cashew oil, canola oil, soybean oil, avocado oil, walnut oil, grapeseed oil, sunflower oil, medium chain triglycerides, coconut oil, palm kernel oil, carnuba wax, beeswax, paraffin wax, rice bran wax, candelilla wax, sunflower wax, sugarcane wax, propolis wax, shellac wax, and combinations thereof, wherein the at least one oil comprises about 20 wt % to about 40 wt % of a complex comprising from about a 10:1 to about a 1:10 wt/wt ratio of caffeine to tannic acid and optionally comprises about 0.1 wt % to about 10 wt % of one or more stabilizers selected from the group consisting of sorbitan trioleate, stearic acid, ethyl cellulose, polyglycerol polyricinoleate, sucrose, and combinations thereof; and b) an aqueous phase optionally comprising about 5 wt % to about 15 wt % of one or more emulsifiers selected from the group consisting of agar, carrageenan, gellan, gelatin, guar gum, sodium alginate, xanthan gum, gum Arabic, *Quillaja saponaria* saponins, one or more protein derived emulsifiers (for example, whey protein isolate and/or sodium caseinate), and combinations thereof.

In certain embodiments, the emulsions can comprise a) about 6 wt % to about 9 wt % of at least one oil, wherein the at least one oil comprises about 20% to about 40% of a complex comprising from about a 5:1 to about a 1:5 wt/wt ratio of caffeine to tannic acid and optionally comprises about 0.2 wt % to about 9 wt % of one or more stabilizers; and b) an aqueous phase optionally comprising about 8 wt % to about 12 wt % of one or more emulsifiers. In some embodiments, the emulsions can comprise a) about 6% to about 9 wt % of at least one oil selected from the group consisting of ghee, mustard oil, olive oil, rice bran oil, flaxseed oil, groundnut oil, sesame oil, almond oil, cashew oil, canola oil, soybean oil, avocado oil, walnut oil, grapeseed oil, sunflower oil, medium chain triglycerides, coconut oil, palm kernel oil, carnuba wax, beeswax, paraffin wax, rice bran wax, candelilla wax, sunflower wax, sugarcane wax, propolis wax, shellac wax, and combinations thereof, wherein the at least one oil comprises about 20 wt % to about 40 wt % of a complex comprising from about a 5:1 to about a 1:5 wt/wt ratio of caffeine to tannic acid and optionally comprises about 0.2 wt % to about 9 wt % of one or more stabilizers selected from the group consisting of sorbitan trioleate, stearic acid, ethyl cellulose, polyglycerol polyricinoleate, sucrose, and combinations thereof; and b) an aqueous phase optionally comprising about 8 wt % to about 12 wt % of one or more emulsifiers selected from the group consisting of agar, carrageenan, gellan, gelatin, guar gum, sodium alginate, xanthan gum, gum Arabic, *Quillaja saponaria* saponins, one or more protein derived emulsifiers (for example, whey protein isolate and/or sodium caseinate), and combinations thereof.

In certain embodiments, the emulsions can comprise a) about 8% of at least one oil, wherein the at least one oil comprises about 30 wt % of a complex comprising about a 1:3 wt/wt ratio of caffeine to tannic acid and comprises from about 0.2 wt % to about 9 wt % of one or more stabilizers; and b) an aqueous phase comprising from about 10 wt % of one or more emulsifiers. In some embodiments, the emulsions can comprise a) about 8 wt % of at least one oil selected from the group consisting of sunflower oil, medium chain triglycerides, and carnuba wax, wherein the at least one oil comprises about 30 wt % of a complex comprising about 1:3 wt/wt ratio of caffeine to tannic acid and comprises about 0.2 wt % to about 9 wt % of one or more stabilizers selected from the group consisting of sorbitan trioleate, stearic acid, ethyl cellulose, polyglycerol polyricinoleate, and combinations thereof; and b) an aqueous phase comprising 10 wt % gum Arabic.

In certain embodiments, the emulsions can comprise a) about 8% of at least one oil, wherein the at least one oil comprises about 30 wt % of a complex comprising about a 1:1 wt/wt ratio of caffeine to tannic acid and comprises from about 0.2 wt % to about 9 wt % of one or more stabilizers; and b) an aqueous phase comprising from about 10 wt % of one or more emulsifiers. In some embodiments, the emulsions can comprise a) about 8 wt % of at least one oil selected from the group consisting of sunflower oil, medium chain triglycerides, and carnuba wax, wherein the at least one oil comprises about 30 wt % of a complex comprising about 1:1 wt/wt ratio of caffeine to tannic acid and comprises about 0.2 wt % to about 9 wt % of one or more stabilizers selected from the group consisting of sorbitan trioleate, stearic acid, ethyl cellulose, polyglycerol polyricinoleate, and combinations thereof; and b) an aqueous phase comprising 10 wt % gum Arabic.

Processes

In certain embodiments, the caffeine-tannic acid complex can be prepared by adding a solution of tannic acid in an appropriate concentration in water to a solution of caffeine in an appropriate concentration in water while mixing under high shear conditions to form a precipitate, and then isolating, drying and grinding the precipitate. Typically the amount of tannic acid added to the water is based on its solubility at a given temperature such that the entire amount of tannic acid is soluble in the amount of water being used. In some embodiments, the tannic acid can be added to water at room temperature. In some embodiments, the tannic acid can be added to water at about 60° C. Similarly, the amount of caffeine initially added to the water is based on its solubility at a given temperature such that the entire amount of caffeine is soluble in the amount of water being used. In some embodiments, the caffeine can be added to water at room temperature. In some embodiments, the caffeine can be added to water at about 60° C.

In some embodiments, the caffeine-tannic acid complex can be prepared by adding the appropriate amount of tannic acid and the appropriate amount of caffeine to absolute ethanol or ethanol containing 0.1%-60% w/w water, stirring until a solution is formed, and then spray-drying the resulting solution. In some embodiments, the ethanol can comprise from about 0.5% to about 55% w/w water. In some embodiments, the ethanol can comprise from about 1% to about 50% w/w water. In some embodiments, the ethanol can comprise from about 2% to about 40% w/w water. In some embodiments, the ethanol can comprise from about 3% to about 30% w/w water. In some embodiments, the ethanol can comprise from about 4% to about 20% w/w water. In some embodiments, the ethanol can comprise from about 0.1%, about 0.5%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, or about 80% w/w water.

In certain embodiments, for purposes of preparing the emulsions described herein, the precipitate can be ground to a small powder and passed through a sieve. In certain embodiments the sieve used can be a 40 mesh sieve. In some embodiments, the resulting powder can be passed through a Jet Mill before preparing an emulsion.

In some embodiments, the emulsions provided herein can be prepared by adding the caffeine-tannic acid complex to at least one oil. In some embodiments, where the oil phase comprises a stabilizer, it can be added to the mixture of oil and caffeine-tannic acid complex. In some embodiments, the oil, the stabilizer, and complex can be combined in a grinding chamber and the resulting mixture can be further treated with non-reactive grinding balls, such as zirconium oxide grinding balls. In some embodiments, the grinding balls can be about 2 mm in diameter, but other diameter balls can be used as appropriate. In some embodiments, the grinding balls can be about 0.5 mm, about 1 mm, or about 2 mm in diameter. In some embodiments, the mixture can be ground in the chamber for about 1 to about 50 hours. In some embodiments, the mixture can be ground in the chamber for about 1 to about 24 hours. In some embodiments, the mixture can be ground in the chamber for about 1 to about 20 hours. In some embodiments, the mixture can be ground in the chamber for about 1 to about 15 hours. In some embodiments, the mixture can be ground in the chamber for about 1 to about 10 hours. In some embodiments, the mixture can be ground in the chamber for about 1 to about 8 hours. In some embodiments, the mixture can be ground in the chamber for about 1 to about 6 hours. In some embodiments, the mixture can be ground in the chamber for about 1 to about 4 hours. In some embodiments, the mixture can be ground in the chamber for about 24 to about 50 hours. In some embodiments, the mixture can be ground in the chamber for about 30 to about 45 hours. In some embodiments, the mixture can be ground in the chamber for about 35 to about 40 hours. In some embodiments, the mixture can be ground at about 500 to about 2000 rpm. In some embodiments, the mixture can be ground at about 500 to about 1500 rpm In some embodiments, the mixture can be ground at about 750 to about 1250 rpm. In some embodiments, the mixture can be ground at about 900 to about 1100 rpm. In some embodiments, the mixture can be ground at about 1000 rpm. In some embodiments, the mixture can be ground in the chamber at a temperature of about 15° C. to about 90° C. In some embodiments, the mixture can be ground in the chamber at a temperature of about 15° C. to about 75° C. In some embodiments, the mixture can be ground in the chamber at a temperature of about 15° C. to about 60° C. In some embodiments, the mixture can be ground in the chamber at a temperature of about 15° C. to about 50° C. In some embodiments, the mixture can be ground in the chamber at a temperature of about 18° C. to about 35° C. In some embodiments, the mixture can be ground in the chamber at a temperature of about 20° C. to about 30° C. Typically, and in some embodiments, the resulting slurry can be separated from the grinding balls.

In certain embodiments, where the emulsions comprises an emulsifier, it can be added to the aqueous phase prior to emulsification. In some embodiments, the aqueous phase can be prepared by slowly adding one or more emulsifiers to heated water. In some embodiments, the water can be heated to a temperature of about 40° C. to about 60° C. In some embodiments, the water can be heated to a temperature of about 50° C. In some embodiments, the mixture can be cooled after the addition.

In some embodiments, the resulting oil phase and the aqueous phase can be combined and emulsified. In certain embodiments, the oil phase can be added to the aqueous phase. In other embodiments, the aqueous phase can be added to the oil phase. In certain embodiments, the oil phase and aqueous phase can be combined at the same time at the same rate, or at different rates. In some embodiments, the combined oil and aqueous phases can be mixed under high speed. In some embodiments, the combined oil and aqueous phases can be mixed on a high shear mixer. In some embodiments, the combined oil and aqueous phases can be mixed at about 10,000 to about 30,000 rpm. In some embodiments, the combined oil and aqueous phases can be mixed at about 15,000 to about 25,000 rpm. In some embodiments, the combined oil and aqueous phases can be mixed at about 20,000 rpm. In some embodiments, the combined oil and aqueous phases can be mixed for about 30 seconds to about 5 minutes. In some embodiments, the combined oil and aqueous phases can be mixed for about 1 minute.

Beverages

The present disclosure also provides beverage syrups and beverages comprising the emulsions disclosed herein. For example, and in some embodiments, a beverage can contain a volume of one or more of the emulsions described herein sufficient to provide a caffeine concentration in the beverage from about 50 ppm to about 900 ppm. In some embodiments, the caffeine concentration in the beverage can be from about from about 75 ppm to about 850 ppm, from about 100 ppm to about 800 ppm, from about 125 ppm to about 750 ppm, from about 150 ppm to about 700 ppm, from about 175 ppm to about 650 ppm, from about 200 ppm to about 550 ppm of caffeine, or from about 225 ppm to about 500 ppm. In some embodiments, the caffeine concentration in the beverage can be about 50 ppm, about 75 ppm, about 100 ppm, about 125 ppm, about 150 ppm, about 175 ppm, about 200 ppm, about 225 ppm, about 250 ppm, about 275 ppm, about 300 ppm, about 325 ppm, about 350 ppm, about 375 ppm, about 400 ppm, about 425 ppm, about 450 ppm, about 475 ppm, about 500 ppm, about 525 ppm, about 550 ppm, about 575 ppm, about 600 ppm, about 625 ppm, about 650 ppm, about 675 ppm, about 700 ppm, about 725 ppm, about 750 ppm, about 775 ppm, or about 800 ppm. In some embodiments, the concentration of caffeine in the beverage can be about 400 ppm.

In certain embodiments, a portion of the caffeine remains bound to the tannic acid for about 30 minutes to about 180 minutes after the beverage is consumed. In some embodiments, a portion of the caffeine remains bound to the tannic acid for about 45 minutes to about 150 minutes, or about 60 minutes to about 120 minutes after the beverage is consumed. In some embodiments, a portion of the caffeine remains bound to the tannic acid for about 30 minutes, about 40 minutes, about 50 minutes, about 60 minutes, about 70 minutes, about 80 minutes, about 90 minutes, about 100 minutes, about 120 minutes, about 130 minutes, about 140 minutes, about 150 minutes, about 160 minutes, about 170 minutes, or about 180 minutes after the beverage is consumed.

In certain embodiments, the percentage of caffeine bound to the tannic acid 90 minutes after consuming the beverage can be from about 50% to about 99%. In some embodiments, the percentage of caffeine bound to the tannic acid can be from about 65% to about 95%, from about 70% to about 90%, or from about 75% to about 85%. In some embodiments, about 50%, about 55%, about 60%, about 65%, about 70%, about 75%, about 80%, about 85%, about 90%, about 95%, or about 99% of the caffeine is bound to the tannic acid 90 minutes after the beverage is consumed.

In certain embodiments, the beverage can be a carbonated or non-carbonated soft drink, a fountain beverage, a frozen ready-to-drink beverage, a coffee, a tea or other brewed beverage, a dairy beverage, a flavored water, an enhanced water, a juice such as a fruit juice (including diluted and ready-to-drink concentrated juices), a fruit juice-flavored drink, a sport drink, a smoothie, a functionally enhanced beverage such as an energy drink, or an alcoholic beverage. In particular embodiments, the beverage can be a carbonated soft drink. In some embodiments, the beverage can be a caffeinated water.

In certain embodiments, the beverages can comprise one or more sweeteners. Sweeteners of beverage embodiments include caloric carbohydrate sweeteners, natural high-potency sweeteners, synthetic high-potency sweeteners, other sweeteners, and combinations thereof.

Examples of suitable caloric carbohydrate sweeteners include sucrose, fructose, glucose, erythritol, maltitol, lactitol, sorbitol, mannitol, xylitol, D-tagatose, trehalose, galactose, rhamnose, cyclodextrin (e.g., α-cyclodextrin, β-cyclodextrin, and λ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, glucuronic acid, gluconic acid, glucono-lactone, abequose, galactosamine, xylo-oligosaccharides (xylotriose, xylobiose and the like), gentiooligoscaccharides (gentiobiose, gentiotriose, gentiotetraose and the like), galacto-oligosaccharides, sorbose, nigerooligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, and glucose syrup.

As used herein, the phrase "natural high-potency sweetener," includes, but is not limited to, rebaudioside A, rebaudioside B, rebaudioside C (dulcoside B), rebaudioside D, rebaudioside E, rebaudioside F, rebaudioside H, rebaudioside I, rebaudioside J, rebaudioside K, rebaudioside L, rebaudioside M, rebaudioside N, rebaudioside O, rebaudioside R, rebaudioside S, rebaudioside T, rebaudioside U, rebaudioside V, dulcoside A, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobtain, baiyunoside, osladin, polypodoside A, pterocaryoside A, pterocaryoside B, mukurozioside, phlomisoside I, periandrin I, abrusoside A, and cyclocarioside I.

Natural high potency sweeteners also include modified natural high potency sweeteners. Modified natural high potency sweeteners include natural high potency sweeteners which have been altered naturally. For example, a modified natural high potency sweeteners include, but are not limited to, natural high potency sweeteners that have been fermented, contacted with enzyme, derivatized, or substituted. In one embodiment, at least one modified natural high potency sweeteners can be used in combination with at least one natural high potency sweeteners. In another embodiment, at least one modified natural high potency sweeteners can be used without a natural high potency sweeteners. Modified natural high potency sweeteners can be substituted for a natural high potency sweeteners or can be used in combination with natural high potency sweeteners for any of the embodiments described herein.

As used herein, the phrase "synthetic sweetener" refers to any composition that is not found in nature and is a high potency sweetener. Non-limiting examples of synthetic sweeteners suitable for embodiments of this invention include, but are not limited to, sucralose, acesulfame potassium, aspartame, alitame, saccharin, neohesperidin dihydrochalcone, cyclamate, neotame, N-[3-(3-hydroxy-4-methoxyphenyl)propyl]-L-a-aspartyl]-L-phenylalanine 1-methyl ester, N-[3-(3-hydroxy-4-methoxyphenyl)-3-methylbutyl]-L-a-aspartyl]-Lphenylalanine 1-methyl ester, N-[3-(3-methoxy-4-hydroxyphenyl)propyl]-L-aaspartyl]-L-phenylalanine 1-methyl ester, salts thereof (as appropriate), and combinations thereof.

Carbon dioxide can be used to provide effervescence to certain embodiments of the beverages disclosed here. Any of the techniques and carbonating equipment known in the art for carbonating beverages can be employed. Carbon dioxide can enhance beverage taste and appearance and cam aid in safeguarding beverage purity by inhibiting and/or destroying objectionable bacteria. In certain embodiments, for example, the beverage can have a $CO_2$ level up to about 4.0 volumes carbon dioxide. Other embodiments can have, for example, from about 0.5 to about 5.0 volumes of carbon dioxide. As used herein, one volume of carbon dioxide refers to the amount of carbon dioxide absorbed by a given quantity of a given liquid, such as water, at 60° F. (16° C.) and one atmospheric pressure. A volume of gas occupies the same space as does the liquid by which it is dissolved. The carbon dioxide content can be selected by those skilled in the art based on the desired level of effervescence and the impact of the carbon dioxide on the taste or mouthfeel of the beverage.

In some embodiments, the beverage can further include additional ingredients, including, generally, any of those typically found in beverage compositions. Examples of such additional ingredients include, but are not limited to, caramel and other coloring agents or dyes, foaming or antifoaming agents, gums, emulsifiers, tea solids, cloud components, and mineral and non-mineral nutritional supplements. Examples of non-mineral nutritional supplement ingredients are known to those of ordinary skill in the art and include, for example, antioxidants and vitamins, including Vitamins A, D, E (tocopherol), C (ascorbic acid), B (thiamine), B2 (riboflavin), B6, B12, K, niacin, folic acid, biotin, and combinations thereof. The optional non-mineral nutritional supplements are typically present in amounts generally accepted under good manufacturing practices. Exemplary amounts can be between about 1% and about 100% Recommended Daily Value (RDV), where such RDVs are established. In certain exemplary embodiments the non-mineral nutritional supplement ingredient(s) can be present in an amount of from about 5% to about 20% RDV, where established.

In certain embodiments, the beverages can also include one or more preservatives. Solutions with a pH below 4 and especially those below 3 typically are "micro-stable," i.e., they resist growth of microorganisms, and so are suitable for longer term storage prior to consumption without the need for further preservatives. However, an additional preservative system can be used if desired. As used here, the terms "preservative system" or "preservatives" include all suitable preservatives approved for use in beverage compositions, including, without limitation, such known chemical preservatives as benzoates, such as sodium, calcium, and potassium benzoate, sorbates, such as sodium, calcium, and potassium sorbate, citrates, such as sodium citrate and potassium citrate, polyphosphates, such as sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives can be used in amounts not exceeding mandated maximum levels under applicable laws and regulations. In some embodiments, the beverages can include potassium sorbate.

In certain embodiments, the beverages can include an antioxidant selected from the group consisting of rutin, quercetin, flavonones, flavones, dihydroflavonols, flavonols, flavandiols, leucoanthocyanidins, flavonol glycosides, flavonone glycosides, isoflavonoids, and neoflavonoids. In particular, the flavonoids may be, but not limited to, quercetin, eriocitrin, neoeriocitrin, narirutin, naringin, hesperidin, hesperetin, neohesperidin, neoponcirin, poncirin, rutin, isorhoifolin, rhoifolin, diosmin, neodiosmin, sinensetin, nobiletin, tangeritin, catechin, catechin gallate, epigallocatechin, epigallocatechin gallate, oolong tea polymerized polyphenol, anthocyanin, heptamethoxyflavone, daidzin, daidzein, biochaminn A, prunetin, genistin, glycitein, glycitin, genistein, 6,7,4' trihydroxy isoflavone, morin, apigenin, vitexin, balcalein, apiin, cupressuflavone, datiscetin, diosmetin, fisetin, galangin, gossypetin, geraldol, hinokiflavone, primuletin, pratol, luteolin, myricetin, orientin, robinetin, quercetagetin, and hydroxy-4-flavone.

The beverages described herein can also optionally include one or more suitable food grade acids. Exemplary acids are water soluble organic acids and their salts and include, but are not limited to, phosphoric acid, sorbic acid, ascorbic acid, benzoic acid, citric acid, tartaric acid, propionic acid, butyric acid, acetic acid, succinic acid, glutaric acid, maleic acid, malic acid, valeric acid, caproic acid, malonic acid, aconitic acid, potassium sorbate, sodium benzoate, sodium citrate, amino acids, and combinations of any of them. In particular embodiments, the beverages include malic acid and/or phosphoric acid.

In some embodiments, the emulsions can be used to prepare beverages. In some embodiments, the emulsions can be added to a beverage syrup which can be diluted to provide a beverage. In some embodiments, the emulsions can be added to a pre-prepared beverage.

The embodiments described herein are further detailed with reference to the examples shown below. These examples are provided for the purpose of illustration only and the embodiments described herein should in no way be construed as being limited to these examples. Rather, the embodiments should be construed to encompass any and all variations which become evident as a result of the teachings provided herein.

EXAMPLES

Example 1A: General Procedure for Preparing Caffeine-Tannic Acid Complex

Tannic acid was added to water and agitated until fully dissolved. In a separate container, caffeine was added to water, and agitated until fully dissolved. The caffeine solution (1.5% w/w aqueous solution) was placed under 3000 rpm shear, and treated with the tannic acid solution (either 1 or 3 equivalents of 1.5% w/w tannic acid solution, depending on the complex being formed) at a rate of 200 g/min. For analysis purposes, the mixture was equilibrated overnight and analysis was performed using the procedure described in Example 2.

To isolate the solid complex, the precipitate was collected by filtration, dried, and ground by hand before being passed through a 40 mesh sieve. The resulting powder was optionally passed through a Jet Mill (Fluid Energy Processing and Equipment Company, Model 00 Jet-O-Mizer system) according to manufacture specified procedure.

Example 1B: Preparation of Caffeine-Tannic Acid Complex Using Spray-Drying

A mixture of 150 g tannic acid, 50 g caffeine, and 800 g aqueous ethanol containing 5% w/w water was gently agitated until the solution become transparent. The solution was spray-dried while maintaining the evaporation temperature below 178° C. to avoid caffeine sublimation to provide the caffeine-tannic acid complex.

Example 1C: Alternative Preparation of Caffeine-Tannic Acid Complex Using Spray-Drying A mixture of 150 g tannic acid, 100 g caffeine, and 650 g aqueous ethanol (5% wt/wt), and 100 g water was gently agitated until the solution become transparent. The solution was spray-dried while maintaining the evaporation temperature below 178° C. to avoid caffeine sublimation to provide the caffeine-tannic acid complex.

Example 2: Procedure for Analyzing Caffeine-Tannic Acid Complexes Using Centrifugation Samples of the aqueous caffeine-tannic acid mixture prepared in Example 1 were pipetted into the sample holder of 1) a centrifuge tube with a 1K molecular weight cut off membrane (to remove any water soluble component with molecular weight less than 1 K Da such as free caffeine). The tube was centrifuged (Beckman Coulter Life Science Avanti JE Rotor: JS5.3 swinging bucket rotor) at 5,300 rpm for 30 min in order to filter the sample through the cut off membranes. The filtrate was prepared for Ultra Performance Liquid Chromatography to analyze the amount of free caffeine. The free caffeine content in the filtrate from 3:1 complex preparation was determined to be 230 ppm. The free caffeine content in the filtrate from 1:1 complex preparation was determined to be 1300 ppm.

Samples of a 1:1 wt/wt caffeine:tannic acid and a 1:3 wt/wt caffeine:tannic acid complex were analyzed by FT IR and compared to non-complexed mixtures of the reagents in the same ratios. As shown in FIGS. 1A, 1B, 2A, 2B, and 3, the FT IR spectra of the complexes differ from those of the mixed reagents, further confirming that the caffeine and tannic acid are associated within the complex.

Figure 4:
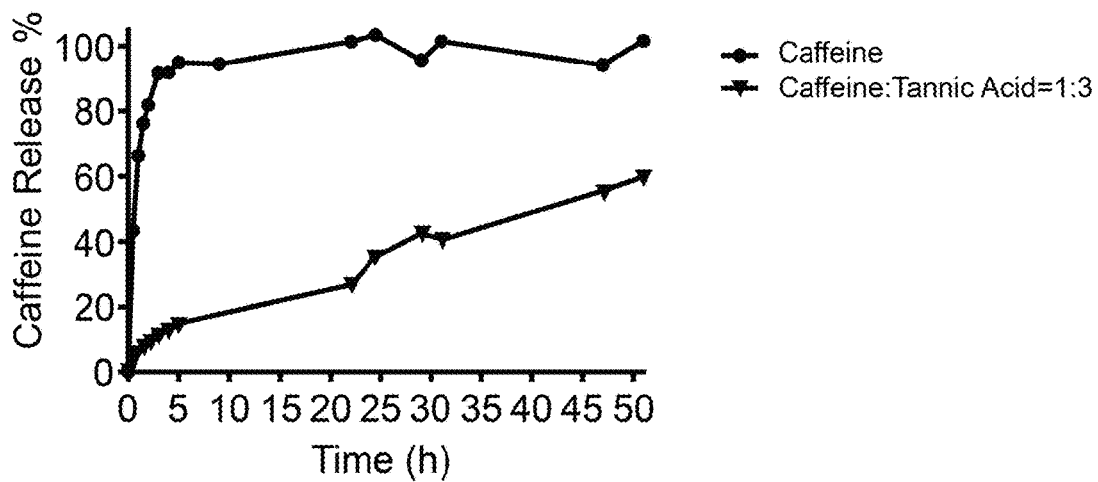
FIG. 4 depicts the rate of caffeine release from caffeine-tannic acid complexes containing varying amounts of tannic acid as determined by dialysis methodology using a dialysis bag with a molecular weight cutoff of 14,000 and by centrifugation

Example 3: Procedure for Determining the Release Rate of Caffeine from Tannic Acid Complexes Using Dialysis Each /caffeine-tannic acid complex (0.2 g) was added to 9.8 g water and put in a dialysis bag and sealed both sides. The bag was placed in beaker containing 90 g of water and gently stirred. At each sampling time, an aliquot was removed from the water outside of the dialysis bag and filtered through a 0.1 μm filter. The caffeine content of the resulting filtrate was analyzed by HPLC. As shown in FIG. 4, all of the caffeine-tannic acid complexes slowed the release of caffeine.

Example 4: General Procedures for Preparing Caffeine-Tannic Acid-Additional Acid Complexes Caffeine (1 g) was added to water (99 g) and stirred until all solids were dissolved. Tannic acid (2 g) and an additional acid (oxalic acid, malonic acid, maleic acid, or citric acid, 3 g) was added to 95 g water and the mixture was stirred until all solids were dissolved. The resulting tannic acid solution was slowly added to the aqueous caffeine solution and the resulting mixture was stirred for 5 minutes, then centrifuged to collect any precipitate. Caffeine release was determined by dialysis as described in Example 5.

Figure 5:
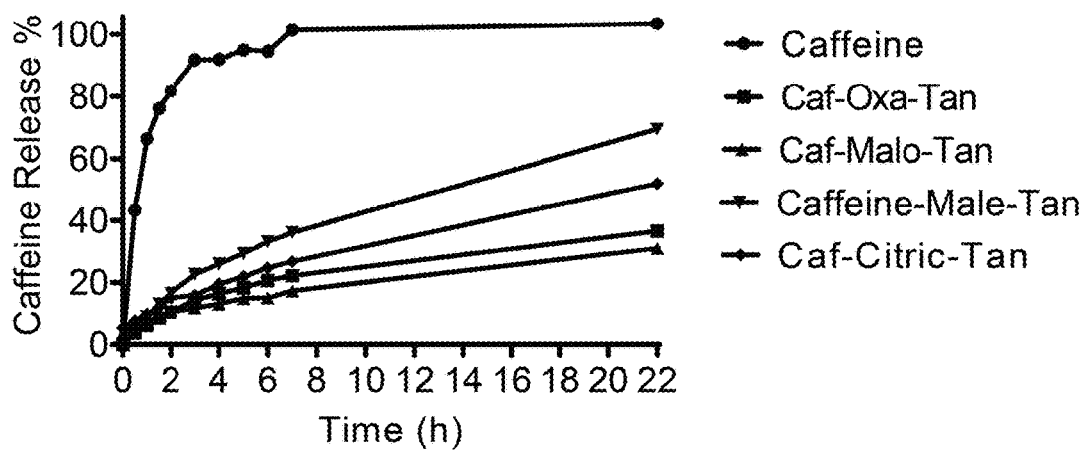
FIG. 5 depicts the rate of caffeine release from complexes comprising tannic acid, caffeine, and an additional organic acid as determined by dialysis methodology using a dialysis bag with a molecular weight cutoff of 14,000.

Example 5: Procedure for Determining the Release Rate of Caffeine from Caffeine-Tannic Acid Complexes Using Dialysis Each complex from Example 4 (0.2 g) and water (9.8 g) was added to a dialysis bag and each end was subsequently sealed. The bag was placed in 90 g water. At each sampling time, an aliquot was removed from the water outside of the dialysis bag and filtered through a 0.1 μm filter. The caffeine content of the resulting filtrate was analyzed by HPLC. Results are shown in FIG. 5. All complexes provided a delayed release of caffeine compared to non-complexed caffeine.

Example 6: Procedures for Preparing
Caffeine-Tannic Acid-Dopamine Complexes

Figure 6:
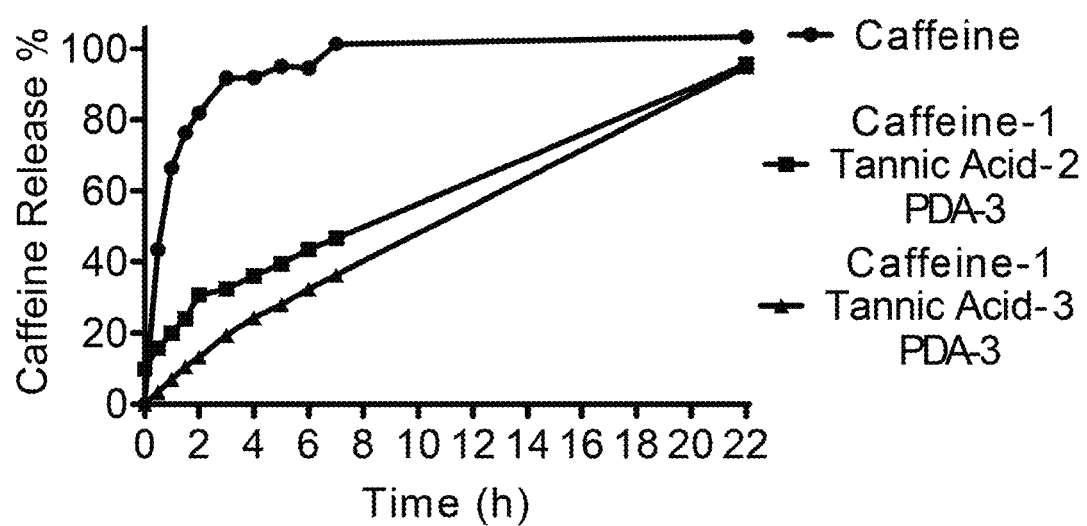
FIG. 6 depicts the rate of caffeine release from complexes comprising tannic acid, caffeine, and varying amounts of dopamine as determined by dialysis methodology using a dialysis bag with a molecular weight cutoff of 14,000.
Figure 7A:
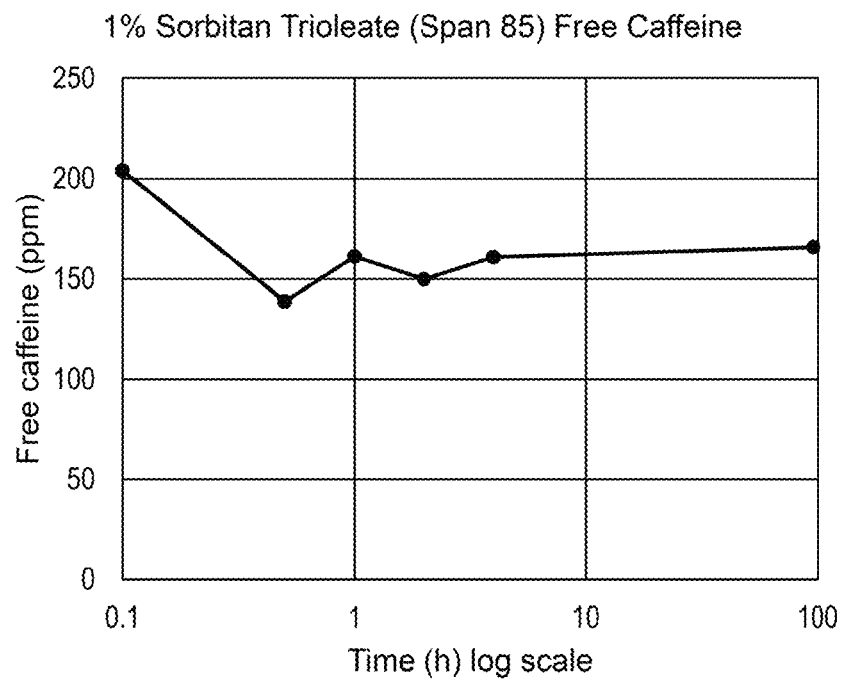
FIG. 7A depicts the change in the amount of free caffeine over time when an emulsion comprising 1% sorbitan trioleate was subjected to dialysis conditions and analyzed using a 1K filter.
Figure 7B:
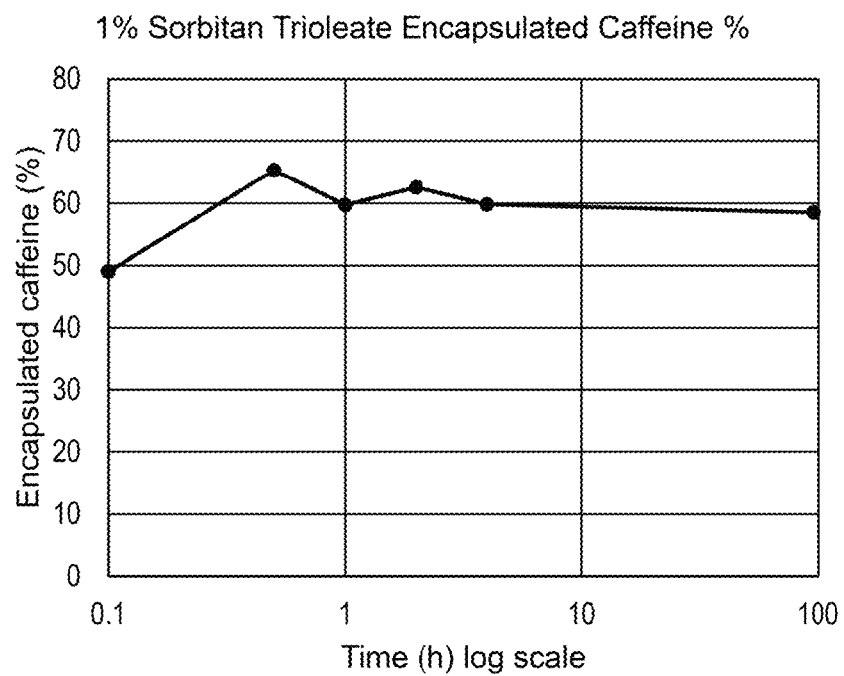
FIG. 7B depicts the change in the amount of encapsulated caffeine over time when an emulsion comprising 1% sorbitan trioleate was subjected dialysis conditions and analyzed using a 1K filter.
Figure 8A:
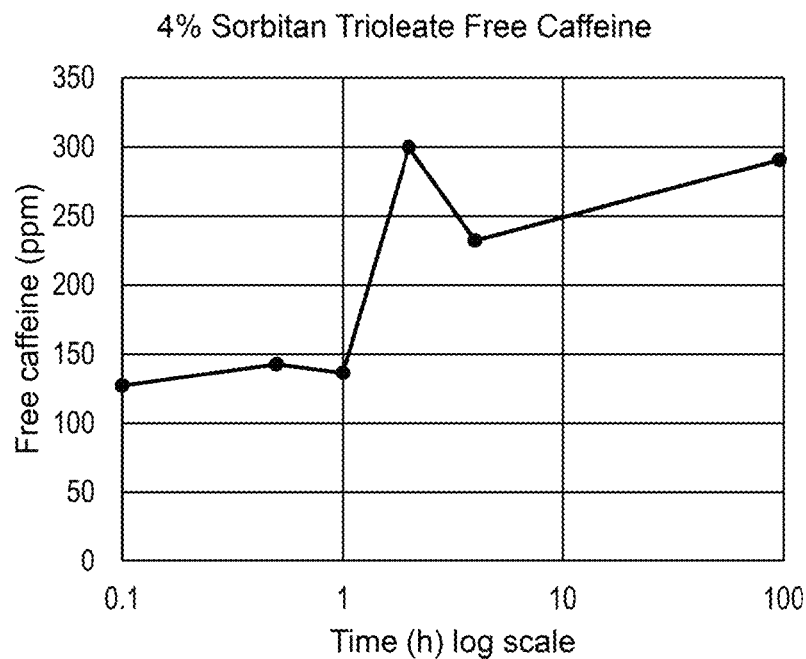
FIG. 8A depicts the change in the amount of free caffeine over time when an emulsion comprising 4% sorbitan trioleate was subjected dialysis conditions and analyzed using a 1K filter.
Figure 8B:
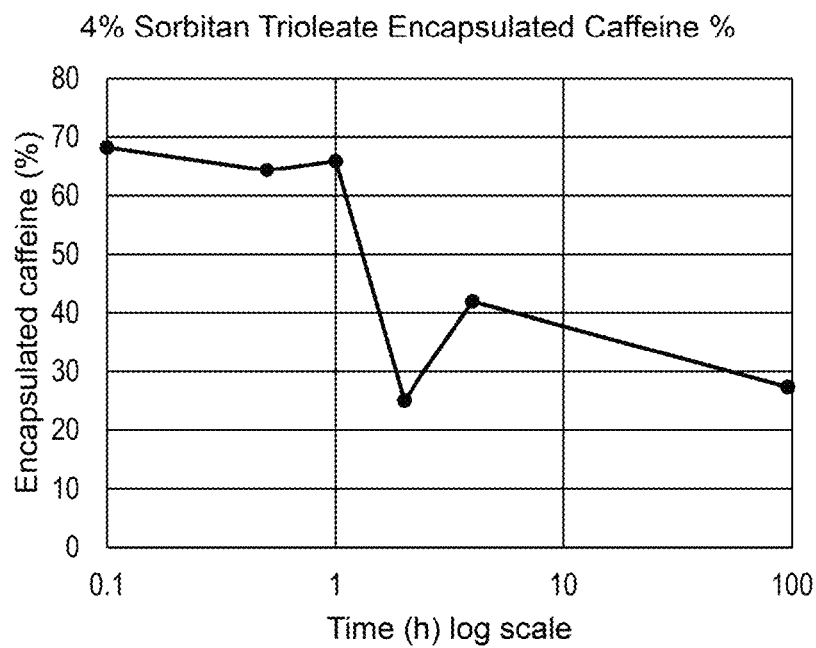
FIG. 8B depicts the change in the amount of encapsulated caffeine over time when an emulsion comprising 4% sorbitan trioleate was subjected dialysis conditions and analyzed using a 1K filter.
Figure 9A:
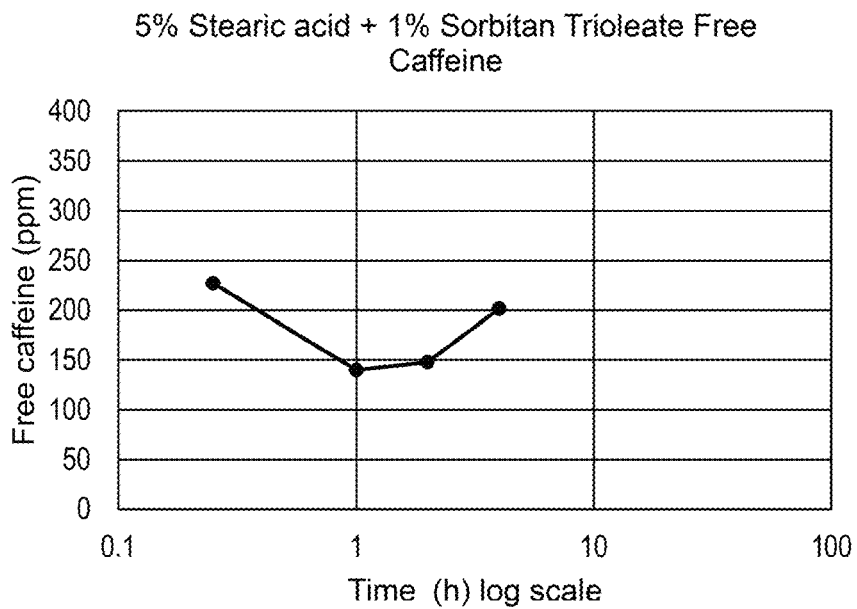
FIG. 9A depicts the change in the amount of free caffeine over time when an emulsion comprising 5% stearic acid and 1% sorbitan trioleate was subjected to dialysis conditions and analyzed using a 1K filter.
Figure 9B:
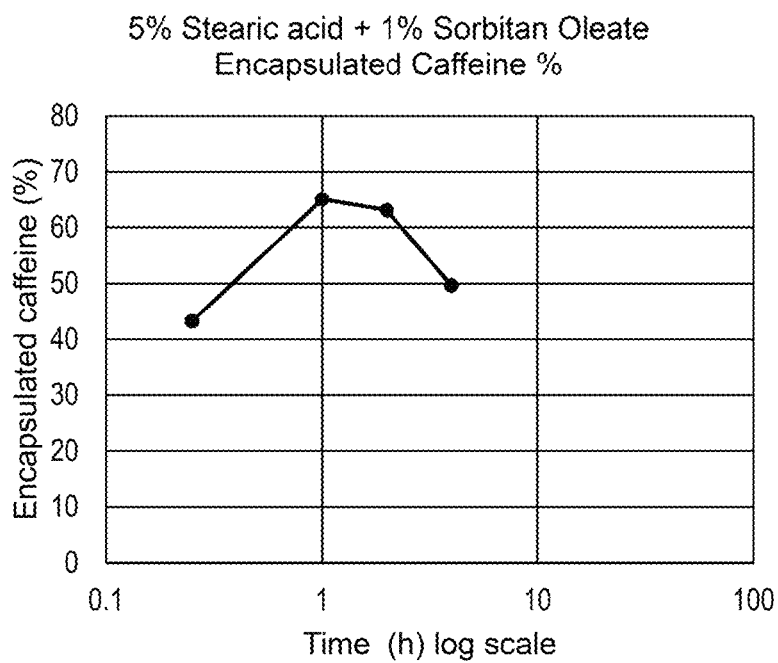
FIG. 9B depicts the change in the amount of encapsulated caffeine over time when an emulsion comprising 5% stearic acid and 1% sorbitan trioleate was subjected to dialysis conditions and analyzed using a 1K filter.
Figure 10A:
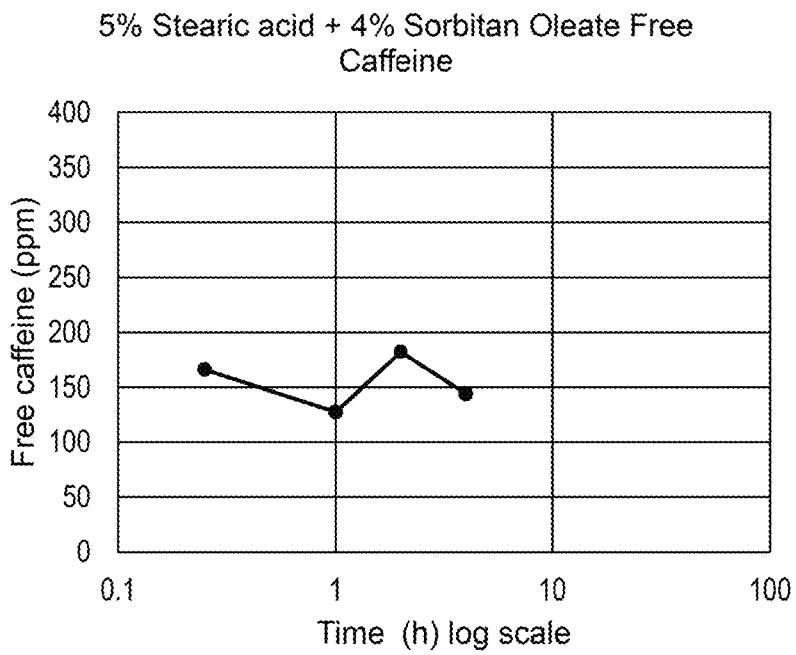
FIG. 10A depicts the change in the amount of free caffeine over time when an emulsion comprising 5% stearic acid and 4% sorbitan trioleate was subjected to dialysis conditions and analyzed using a 1K filter.
Figure 10B:
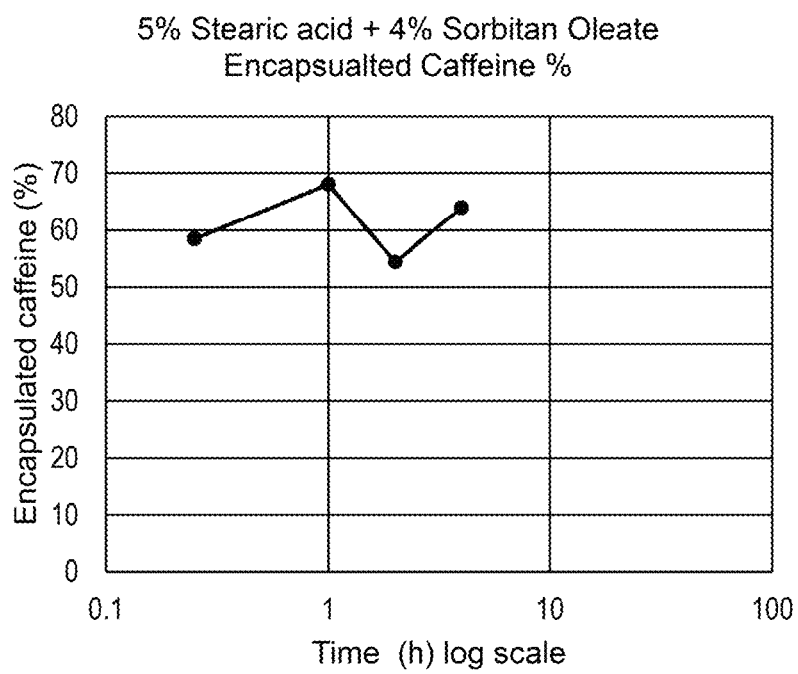
FIG. 10B depicts the change in the amount of encapsulated caffeine over time when an emulsion comprising 5% stearic acid and 4% sorbitan trioleate was subjected to dialysis conditions and analyzed using a 1K filter.
Figure 11A:
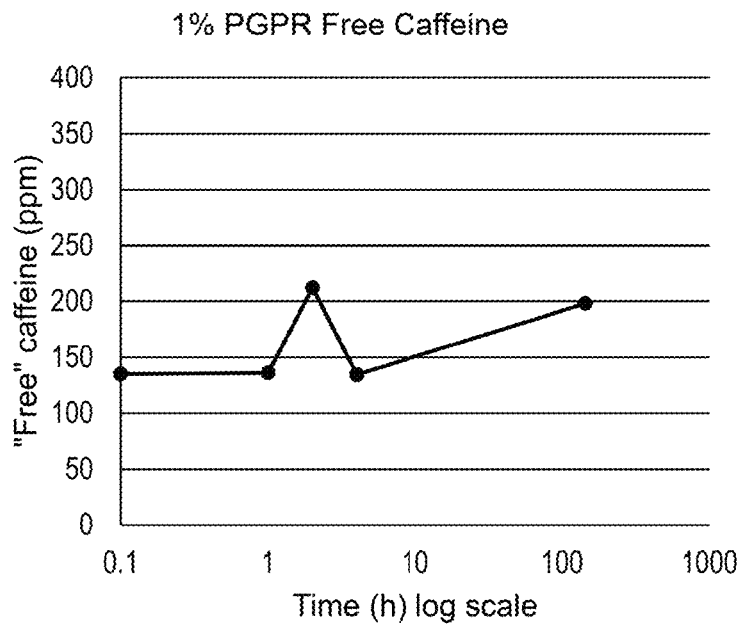
FIG. 11A depicts the change in the amount of free caffeine over time when an emulsion comprising 1% polyglycerol polyricinoleate (PGPR) was subjected to dialysis conditions and analyzed using a 1K filter.
Figure 11B:
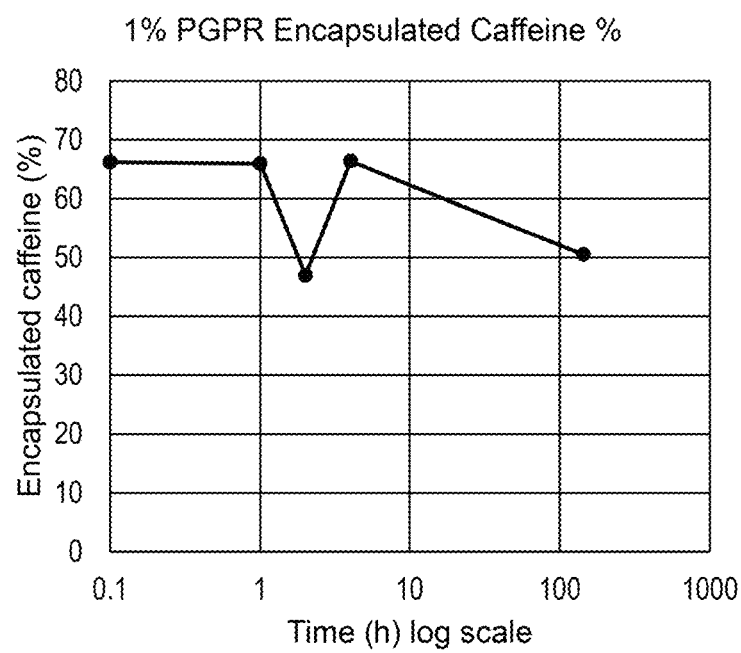
FIG. 11B depicts the change in the amount of encapsulated caffeine over time when an emulsion comprising 1% PGPR was subjected to dialysis conditions and analyzed using a 1K filter.
Figure 12A:
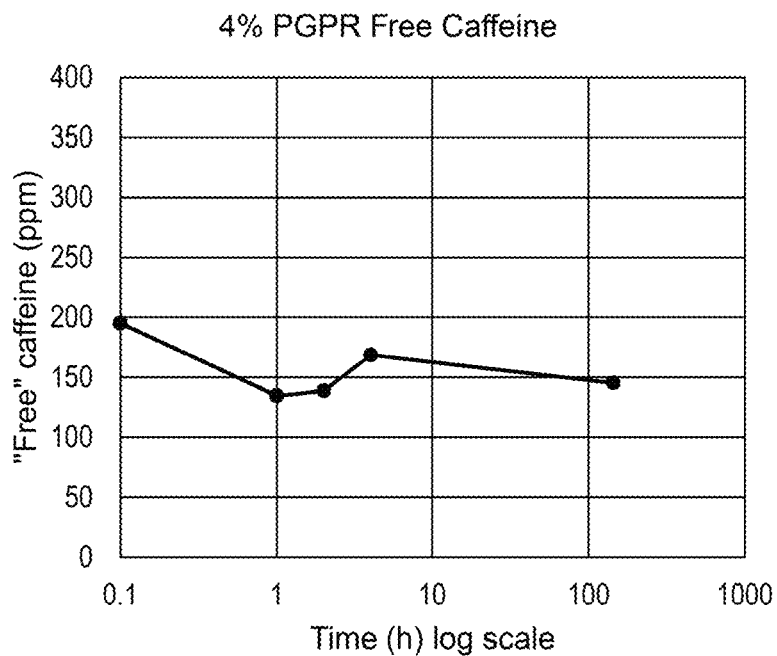
FIG. 12A depicts the change in the amount of free caffeine over time when an emulsion comprising 4% PGPR was subjected to dialysis conditions and analyzed using a 1K filter.
Figure 12B:
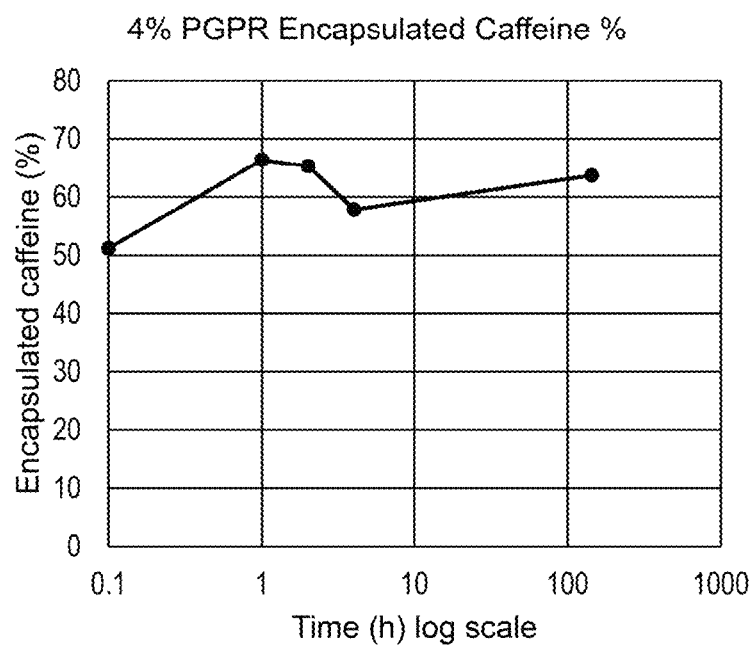
FIG. 12B depicts the amount of encapsulated caffeine over time when an emulsion comprising 4% PGPR was subjected to dialysis conditions and analyzed using a 1K filter.
Figure 13A:
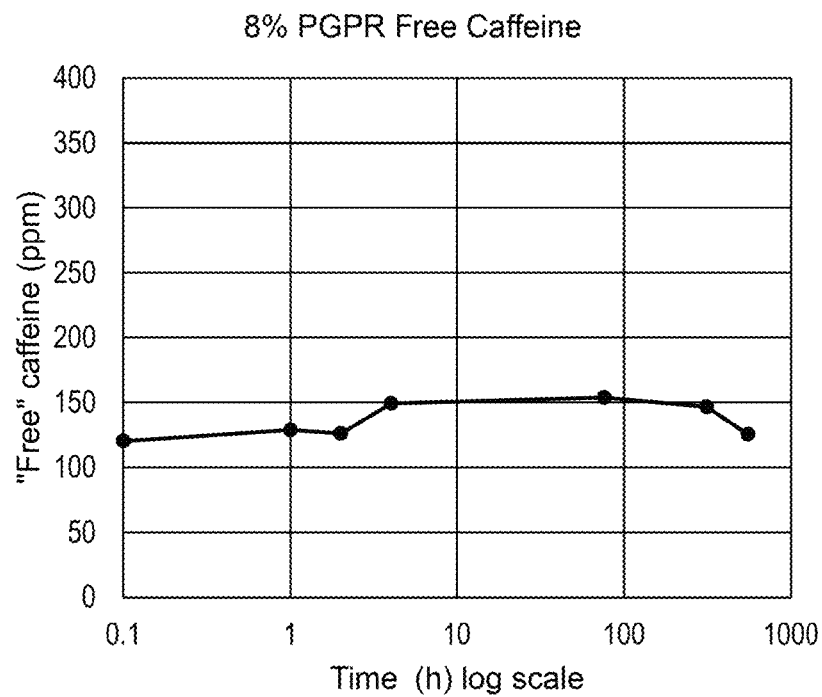
FIG. 13A depicts the change in the amount of free caffeine over time when an emulsion comprising 8% PGPR was subjected to dialysis conditions and analyzed using a 1K filter.
Figure 13B:
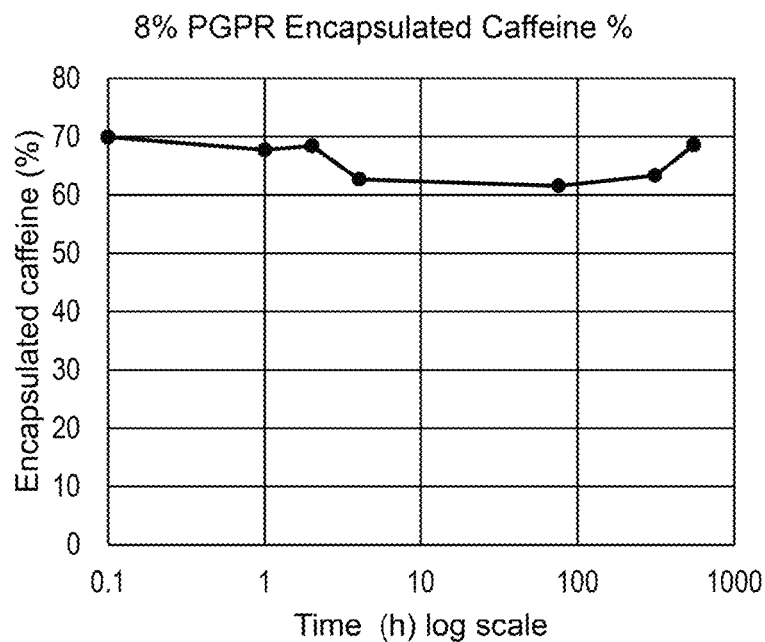
FIG. 13B depicts the amount of encapsulated caffeine over time when an emulsion comprising 8% PGPR was subjected to dialysis conditions and analyzed using a 1K filter.
Figure 14A:
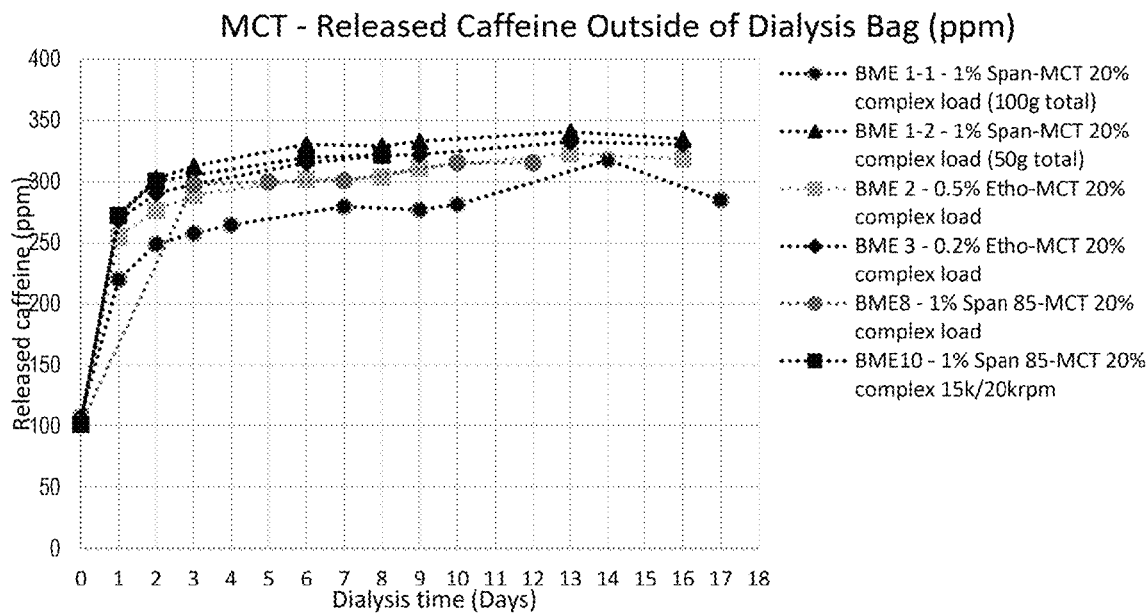
FIG. 14A depicts the change in the amount of free caffeine over time when emulsions comprising medium chain triglycerides were subjected to dialysis conditions using a dialysis bag with a molecular weight cutoff of 14,000.
Figure 14B:
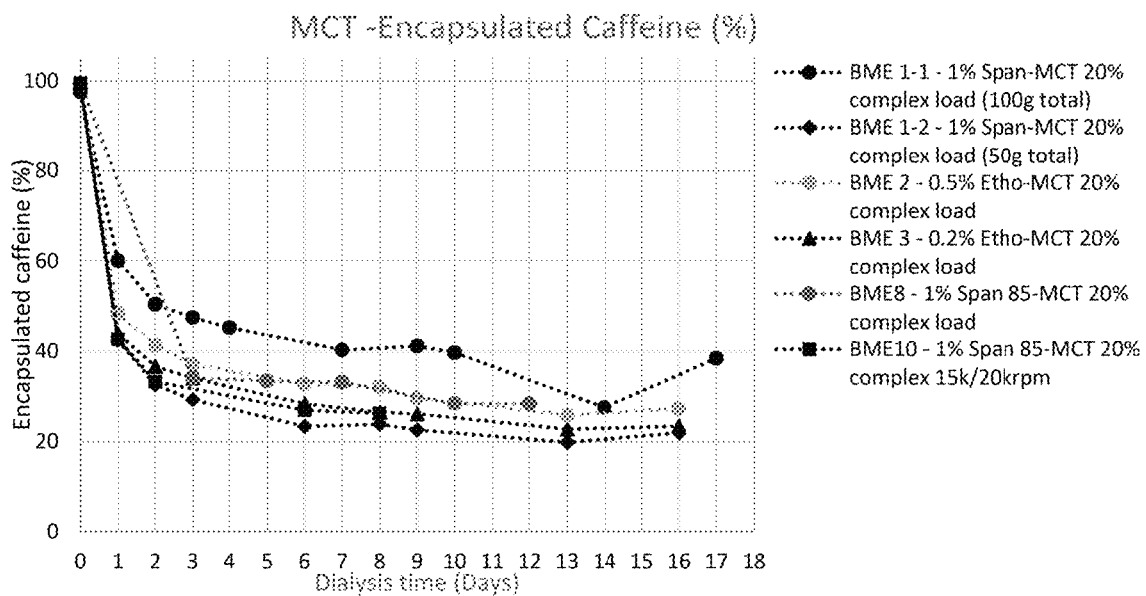
FIG. 14B depicts the amount of encapsulated caffeine over time when emulsions comprising medium chain triglycerides were subjected to dialysis conditions using a dialysis bag with a molecular weight cutoff of 14,000.
Figure 15A:
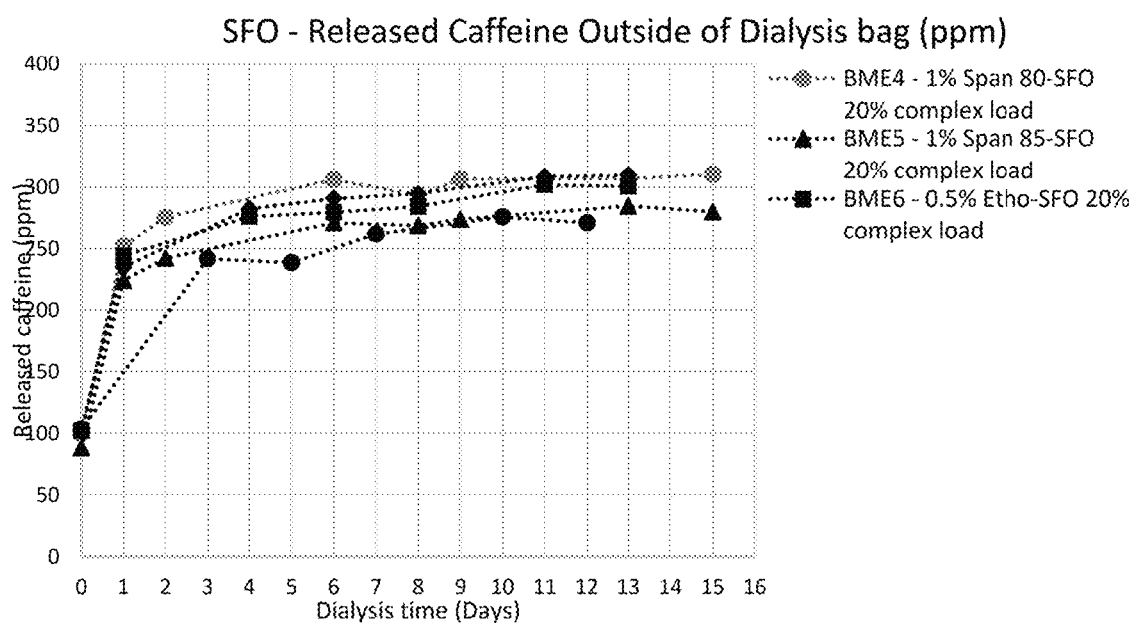
FIG. 15A depicts the amount of encapsulated caffeine over time when emulsions comprising sunflower oil were subjected to dialysis conditions using a dialysis bag with a molecular weight cutoff of 14,000.
Figure 15B:
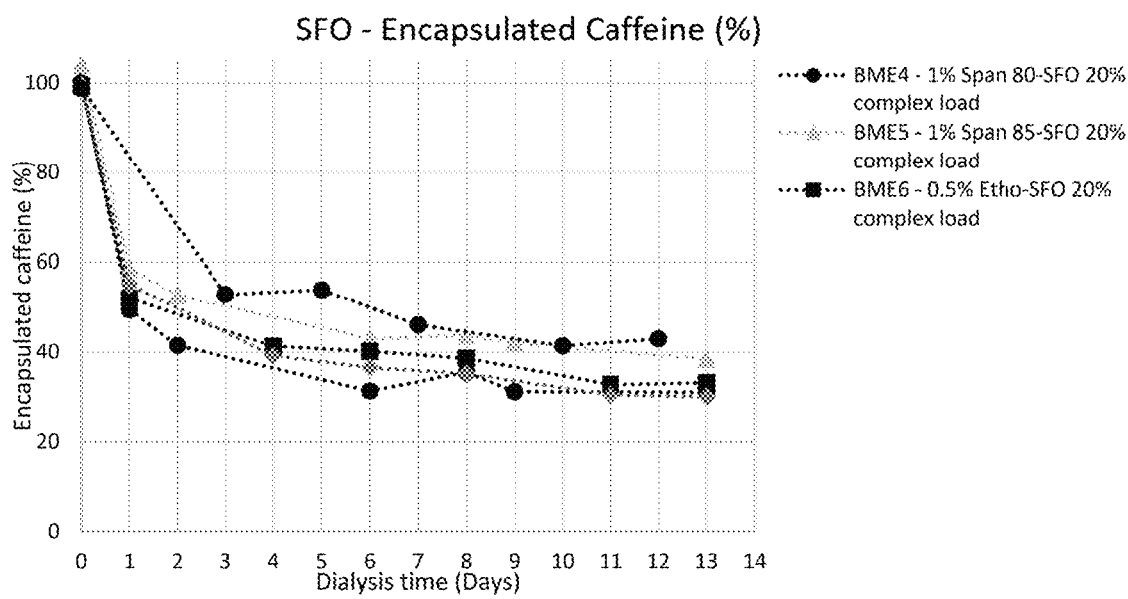
FIG. 15B depicts the amount of caffeine released over time from emulsions comprising sunflower oil subjected to dialysis conditions using a dialysis bag with a molecular weight cutoff of 14,000.
Figure 16:
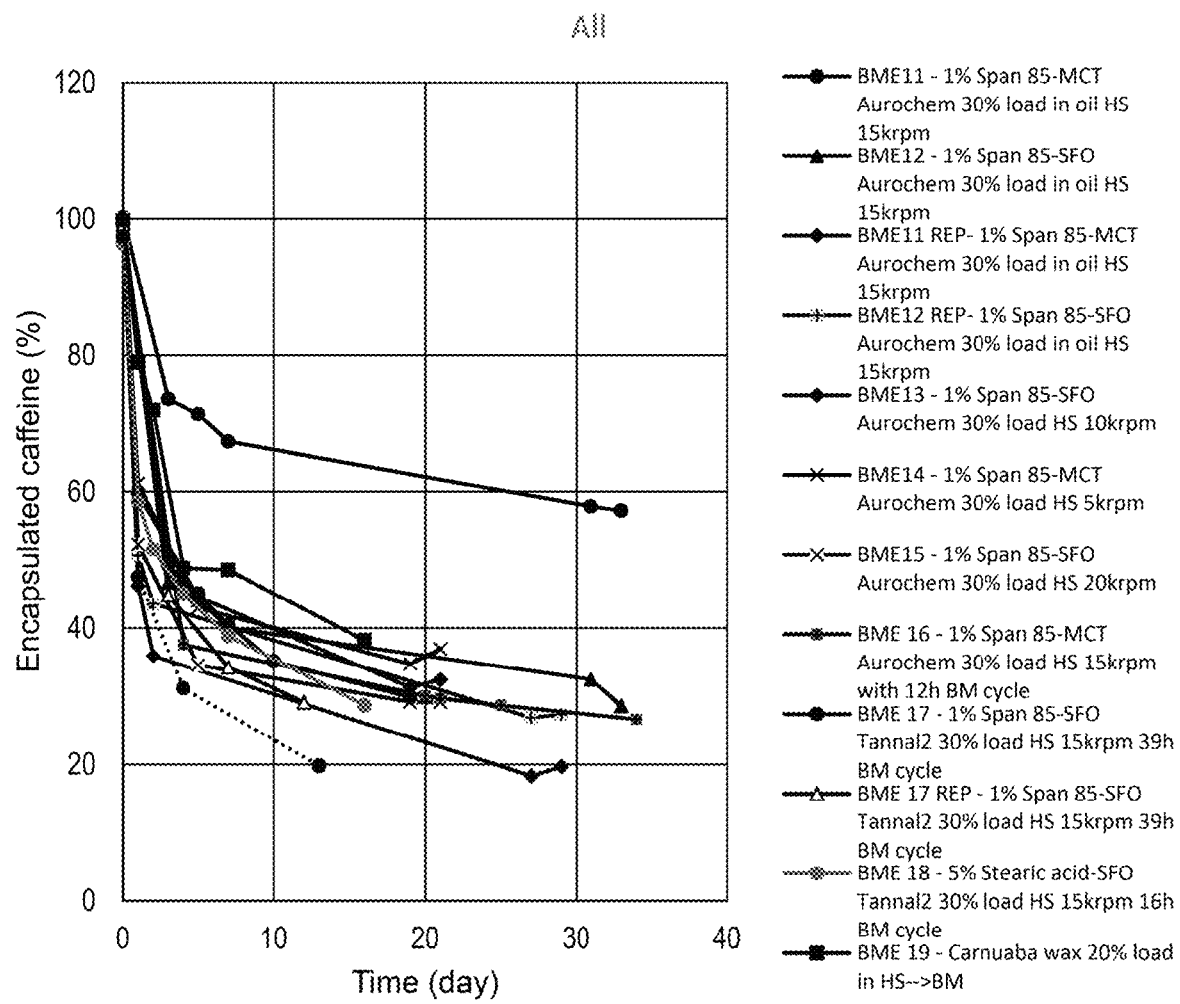
FIG. 16 depicts the amount of encapsulated caffeine over time in various emulsions subjected to dialysis conditions using a dialysis bag with a molecular weight cutoff of 14,000.

Caffeine (1 g) was added to water (99 g) and stirred until all solids were dissolved. Tannic acid (2 g or 3 g) and dopamine (3 g) were added to 95 g water and the mixture was stirred until all solids were dissolved. This solution was slowly added to the aqueous caffeine solution and the resulting mixture was stirred for 5 minutes, then centrifuged to collect any precipitate. Caffeine release was determined by dialysis. Each complex (0.2 g) and water (9.8 g) were added to a dialysis bag each end was sealed. The bag was placed in 90 g water. After 30 minutes, an aliquot was removed from the water outside of the dialysis bag and filtered through a 0.1 μm filter. The caffeine content of the resulting filtrate was analyzed by HPLC. Samples were taken for analysis every 30 minutes for 2 hours, then hourly for an additional 5 hours. As shown in FIG. 6, complexes provided a delayed release of caffeine compared to free caffeine.

Example 7: General Procedure for Preparing
Caffeine-Tannic Acid Emulsions

The caffeine-tannic acid complex from Example 1 was dried, and ground by hand before being passed through a 40 mesh sieve. The resulting powder was optionally passed through Jet Mill (Fluid Energy Processing and Equipment Company, Model 00 Jet-O-Mizer system) according to manufacture specified procedure.

Stabilizer (polyglycerol polyricinoleate, (PGPR)), sorbitan trioleate (Span® 85), sorbitan oleate (Span® 80), or ethyl cellulose (Ethocel®), 1.68 g) was dissolved in oil (sunflower or medium chain triglycerides (MCT), 19.32 g), combined with the jet-milled complex powder (9 g) in a grinding chamber, treated with zirconium oxide grinding balls (Ball Diameter 2 mm, 60 mL), and gently stirred. The grinding chamber was sealed and ground in the ball mill (E-Max 220V) for 39 hrs at 1000 rpm at a temperature of 20° C.-30° C. The resulting slurry was separated from the grinding balls using a vacuum flask and mesh screen.

Deionized water (900 g) was heated to 50° C., slowly treated with 100 g gum Arabic powder, and then cooled down to RT. The oil slurry (4 g) was added to the gum Arabic solution (46 g) with stirring, ensuring that the oil phase had minimal sticking to the apparatus and the container. Once combined, the mixture was placed in a high shear mixer and combined at 20,000 rpm for 1 minute to prepare an emulsion comprising 92% water phase (i.e., 10% gum Arabic solution), and 8% oil phase (i.e, 8% polyglycerol polyricinoleate (PGPR) in sunflower oil, with 30% complex load; ball mill slurry). Net caffeine content: 0.6% w/w. Particle size for the emulsions was determined using a Horiba LA-950 particle size analyzer according to the manufacturer's instructions. The caffeine release profile of the emulsions was determined using the centrifugation method of Example 9 or the dialysis procedure described in Example 8.

Example 8: Procedure for Determining the Release
Rate of Caffeine from Emulsions Using Dialysis A solution of 1% caffeine in pH 3.0 buffer was added to 570 g pH 3.0 buffer to obtain a 100 ppm free caffeine solution. A dialysis bag was prepared with reverse osmosis water. Excess water was removed and the bottom of the bag was folded and clamped. Emulsion (30 g) was added into the dialysis bag and the top of the bag was folded and clamped. A small stir bar was added to a beaker with the caffeinated buffer and the dialysis bag was added to the beaker. The beaker was placed on a stir plate and slowly stirred (<100 rpm). After five minutes a sample of water outside the bag was taken in a syringe fitted with a 0.1 μm filter. The sample was slowly filtered into a glass vial and the filtrate was analyzed by Ultra-Performance Liquid Chromatography to analyze the free caffeine. Parafilm® was placed on top of the system to seal and prevent evaporation. The system was sampled again after 1, 4, 7, and 12 days, then once a week as needed during the shelf life of the emulsion up to about six months.

Table 2 shows emulsions that were prepared and analyzed under dialysis conditions. All emulsions, except where otherwise noted, contain a 92:8 wt/wt ratio of water phase to oil phase and contain 15% gum Arabic in the aqueous phase. The amount of free and encapsulated caffeine over time for representative examples is shown in FIGS. 14A to 16. As shown in FIGS. 14A, 14B, 15A, 15B, and 16, both MCT and sunflower oil provided a steady level of encapsulated caffeine over time.

TABLE 2

| Emulsion Number | Components | Caffeine in Emulsion (ppm) | Caffeine in Oil Phase (ppm) | Tannic Acid Source | Complex Load in Oil | Stabilizer %-Oil Type | High Shear Conditions |
|---|---|---|---|---|---|---|---|
| BME 1-1 | 1% Span 85-MCT 20% complex load (100 g total) | 4000 | 50000 | Sigma | 20% | 1% Span 80-MCT | 10K rpm 1 min |
| BME 1-2 | 1% Span 80-MCT 20% complex load (50 g total) | 4000 | 50000 | Sigma | 20% | 1% Span 80-MCT | 10K rpm 1 min |
| BME 2 | 0.5% ethyl cellulose-MCT 20% complex load | 4000 | 50000 | Sigma | 20% | 0.5% Etho-MCT | 10K rpm 1 min |

TABLE 2-continued

| Emulsion Number | Components | Caffeine in Emulsion (ppm) | Caffeine in Oil Phase (ppm) | Tannic Acid Source | Complex Load in Oil | Stabilizer %-Oil Type | High Shear Conditions |
|---|---|---|---|---|---|---|---|
| BME 3 | 0.2% ethyl cellulose - MCT 20% complex load | 4000 | 50000 | Sigma | 20% | 0.2% Etho-MCT | 10K rpm 1 min |
| BME 4 | 1% sorbitan monooleate-sunflower oil 20% complex load | 4000 | 50000 | Sigma | 20% | 1% Span 80-SFO | 10K rpm 1 min |
| BME 5 | 1% sorbitan trioleate-sunflower oil 20% complex load | 4000 | 50000 | Sigma | 20% | 1% Span 85-SFO | 10K rpm 1 min |
| BME 6 | 0.5% ethyl cellulose - sunflower oil 20% complex load | 4000 | 50000 | Sigma | 20% | 0.5% Etho-SFO | 10K rpm 1 min |
| BME 7 | 0.2% ethyl cellulose - sunflower oil 20% complex load | 4000 | 50000 | Sigma | 20% | 0.2% Etho-SFO | 10K rpm 1 min |
| BME 8 | 1% sorbitan trioleate-MCT 20% complex load | 4000 | 50000 | Sigma | 20% | 1% Span 85-MCT | 10K rpm 1 min |
| BME 9 | 1% sorbitan trioleate-sunflower oil 30% complex load | 6000 | 75000 | Sigma | 30% | 1% Span 85-SFO | 10K rpm 1 min |
| BME 10 | 1% sorbitan trioleate-MCT 20% complex | 4000 | 50000 | Sigma | 20% | 1% Span 85-MCT | 15K/20k rpm 1 + 1 min |
| BME 11 | 1% sorbitan trioleate-MCT 30% complex | 6000 | 75000 | Sigma | 30% | 1% Span 85-MCT | 15K rpm 1 min |
| BME 12 | 1% sorbitan trioleate-sunflower oil 30% complex | 6000 | 75000 | Sigma | 30% | 1% Span 85-SFO | 15K rpm 1 min |
| BME 13 | 1% sorbitan trioleate-sunflower oil 30% load with high shear | 6000 | 75000 | Aurochem | 30% | 1% Span 85-SFO | 10K rpm 1 min |
| BME 14 | 1% sorbitan trioleate-MCT 30% load HS | 6000 | 75000 | Aurochem | 30% | 1% Span 85-MCT | 5K rpm 1 min |
| BME 15 | 1% sorbitan trioleate-sunflower oil 30% load with high shear | 6000 | 75000 | Aurochem | 30% | 1% Span 85-SFO | 20K rpm 1 min |

TABLE 2-continued

| Emulsion Number | Components | Caffeine in Emulsion (ppm) | Caffeine in Oil Phase (ppm) | Tannic Acid Source | Complex Load in Oil | Stabilizer %-Oil Type | High Shear Conditions |
|---|---|---|---|---|---|---|---|
| BME 16 | 1% sorbitan trioleate-MCT 30% load HS 15k rpm with 12 h ball mill cycle | 6000 | 75000 | Aurochem | 30% | 1% Span 85-SFO | 15K rpm 1 min |
| BME 17 | 1% soribtan trioleate-sunflower oil 30% load HS 15k rpm 39 h BM cycle | 6000 | 75000 | Tannal 2 | 30% | 1% Span 85-SFO | 15K rpm 1 min |
| BME 18 | 1% sorbitan trioleate, 5% Stearic acid-sunflower oil, 30% load HS 15k rpm 16 h BM cycle | 6000 | 75000 | Tannal 2 | 30% | 1% Span 85-SFO | 15K rpm 1 min |
| BME 19 | 14.3% Carnuaba wax 20% load in HS-->BM (85.7:14.3 wt/wt ratio of oil phase: water phase) | 7143 | 89286 | Tannal 2 | 20% | 14.3% (carnuaba wax) | 15K rpm 1 min |
| BME 20 | 5 mM CaCl$_2$ complex 1% sorbitan trioleate-sunflower oil 30% load | 6000 | 75000 | Tannal 2 | 30% | 1% Span 85-SFO | 15K rpm 1 min |

Example 9: Procedure for Determining the Release Rate of Caffeine from Emulsions Using Centrifugation For a typical experiment, 10 g of emulsion was mixed with 140 g of pH 3 buffer. At designed sampling time, an aliquot was removed and loaded into a centrifuge tube with 1K molecular weight cut off. The tube was centrifuged at 5,300 rpm for 30 min in order to filter the sample through the cut off membranes. The amount of free and encapsulated caffeine as determined over time for the emulsions shown in Table 3 is shown in FIGS. 7A-13B. As shown in each of the figures, the percentage of encapsulated caffeine (or the amount of free caffeine) remains stable over time.

TABLE 3

| Stabilizer | Oil | Aqueous Phase | Tannic Acid/Caffeine Ratio |
|---|---|---|---|
| 1% sorbitan trioleate (Span ® 85) | Sunflower | 10% gum Arabic | 3:1 |
| 4% sorbitan trioleate (Span ® 85) | Sunflower | 10% gum Arabic | 3:1 |
| 5% stearic acid + 1% sorbitan trioleate (Span ® 85) | Sunflower | 10% gum Arabic | 3:1 |
| 1% PGPR | Sunflower | 10% gum Arabic | 3:1 |
| 4% PGPR | Sunflower | 10% gum Arabic | 3:1 |
| 8% PGPR ("Emulsion A") | Sunflower | 10% gum Arabic | 3:1 |

Example 10: Preparation of Representative Beverage

The ingredients shown below were combined to form citrate buffer:

| Ingredient | Per Liter Batch 3.0 pH |
|---|---|
| Citric Acid | 1.1300 gms |
| Tri Sodium Citrate | 0.1600 gms |
| Sodium Benzoate | 0.1575 gms |
| Water in L (QS to volume) | 1 |

A representative beverage was prepared by diluting the emulsion of 8% PGPR recited in Table 3 15× with citrate buffer (pH 3) to provide a caffeine concentration of 400 ppm.

Figure 17:
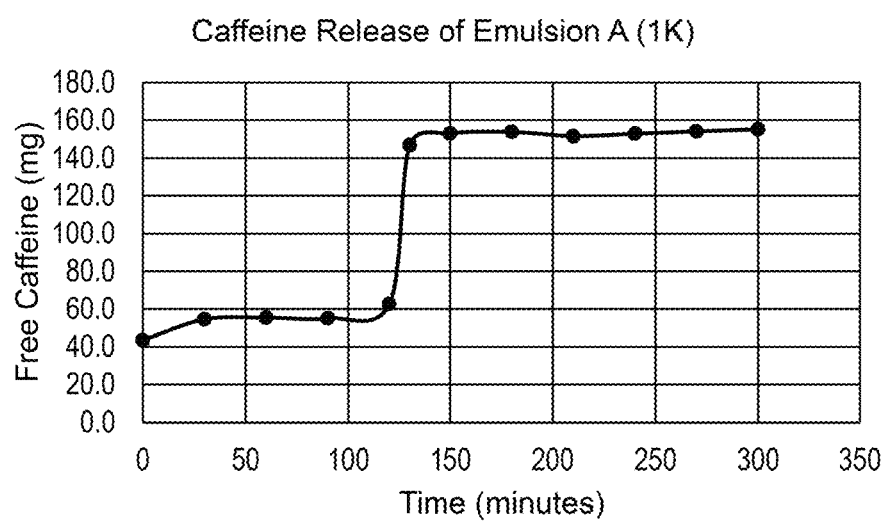
FIG. 17 depicts the amount caffeine released from a representative beverage containing a representative emulsion when subjected to a simulated gastric conditions.

Example 11: Determination of Caffeine Release Profile of Representative Beverage Via Stomach Model Citrate buffer (pH 3, 60 mL), gastric mucosa mucin solution (prepared from 1.5 g gastric mucosa mucin in 50 mL water, 21.5 mL of solution used), and pepsin (0.2% solution, 21.5 mL) were combined and allowed to equilibrate up to 37° C. in a water bath for at least 30 minutes. After the equilibration period, the representative beverage was added, a sample was taken to represent T=0, and 1.5N HCl was pumped in at a rate of 0.25 mL/min. The HCl was added until 30.0 mL had been added or until the pH=<1.8. Samples were taken every 30 minutes. After the pH=<1.8 (approximately 2 hours mark), the pump was stopped. 5N NaOH, NaHCO$_3$, pancreatin, and bile salts were added to simulate the shift to the upper intestine. The mixture was stirred for 3 hours, and sampled every 30 minutes using the centrifugation method described in described in Example 9. Results are shown in FIG. 17. As shown in the graph, the release of the caffeine from the beverage was delayed until the beverage reached the small intestine portion of the model. Note that the T=0 measurement indicates that there was an initial release of caffeine upon either dilution or by addition of the sample to the model.

These results demonstrate that adding the caffeine complexes and emulsions described herein to beverages can delay the release of the caffeine once the beverages are consumed, eliminating the jitteriness and "caffeine crash" sometimes associated with consumption of these beverages.

The breadth and scope of the present disclosure should not be limited by any of the above-described exemplary embodiments, but should be defined only in accordance with the following claims and their equivalents.

All patents, patent applications, and other reference noted or referenced in this application are hereby incorporated by reference in their entirety.

What is claimed is:

1. An emulsion comprising:
   a. an oil phase comprising at least one oil comprising a complex comprising caffeine and tannic acid; and
   b. an aqueous phase comprising water;
   wherein the emulsion comprises from about 2 wt % to about 30 wt % of the at least one oil.

2. The emulsion of claim 1, further comprising one or more stabilizers.

3. The emulsion of claim 1, further comprising one or more emulsifiers.

4. The emulsion of claim 1, wherein the emulsion comprises about 5 wt % to about 10 wt % of the at least one oil.

5. The emulsion of claim 1, wherein the at least one oil is selected from the group consisting of one or more edible oils, one or more edible waxes, and combinations thereof.

6. The emulsion of claim 1, wherein the at least one oil is selected from the group consisting of ghee, mustard oil, olive oil, rice bran oil, flaxseed oil, groundnut oil, sesame oil, almond oil, cashew oil, canola oil, soybean oil, avocado oil, walnut oil, grapeseed oil, sunflower oil, medium chain triglycerides, coconut oil, palm kernel oil, carnuba wax, beeswax, paraffin wax, rice bran wax, candelilla wax, sunflower wax, sugarcane wax, propolis wax, shellac wax, and combinations thereof.

7. The emulsion of claim 1, wherein the at least one oil is selected from the group consisting of sunflower oil and medium chain triglycerides.

8. The emulsion of claim 1, wherein the emulsion comprises from about 0.1 wt % to about 15 wt % of the complex.

9. The emulsion of claim 1, wherein the emulsion comprises from about 1 wt % to about 4 wt % of the complex.

10. The emulsion of claim 2, wherein the emulsion comprises from about 0.002 wt % to about 8 wt % of the one or more stabilizers.

11. The emulsion of claim 2, wherein the emulsion comprises from about 0.08 wt % to about 1.2 wt % of the one or more stabilizers.

12. The emulsion of claim 2, wherein the one or more stabilizers is selected from the group consisting of sorbitan trioleate, stearic acid, ethyl cellulose, polyglycerol polyricinoleate, sucrose, and combinations thereof.

13. The emulsion of claim 2, wherein the one or more stabilizers is selected from the group consisting of sorbitan trioleate, stearic acid, ethyl cellulose, polyglycerol polyricinoleate, and combinations thereof.

14. The emulsion of claim 3, wherein the emulsion comprises from about 4 wt % to about 40 wt % of the one or more emulsifiers.

15. The emulsion of claim 3, wherein the emulsion comprises about 10 wt % of the one or more emulsifiers.

16. The emulsion of claim 3, wherein the one or more emulsifiers is selected from the group consisting of agar, carrageenan, gellan, gelatin, guar gum, sodium alginate, xanthan gum, gum Arabic, *Quillaja saponaria* saponins, and combinations thereof.

17. The emulsion of claim 3, wherein the one or more stabilizers is gum Arabic.

18. A beverage comprising an emulsion of claim 1.

* * * * *